(12) United States Patent
Desai et al.

(10) Patent No.: US 8,644,952 B2
(45) Date of Patent: Feb. 4, 2014

(54) MEDICAL DEVICES INCLUDING POLYISOBUTYLENE BASED POLYMERS AND DERIVATIVES THEREOF

(75) Inventors: Shrojalkumar Desai, Little Canada, MN (US); G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 539 days.

(21) Appl. No.: 12/874,887

(22) Filed: Sep. 2, 2010

(65) Prior Publication Data
US 2011/0054581 A1   Mar. 3, 2011

Related U.S. Application Data

(63) Continuation-in-part of application No. 12/784,559, filed on May 21, 2010, now Pat. No. 8,374,704.

(60) Provisional application No. 61/239,115, filed on Sep. 2, 2009.

(51) Int. Cl.
*A61N 1/05* (2006.01)

(52) U.S. Cl.
USPC .............................. 607/116; 29/874

(58) Field of Classification Search
USPC .............................. 607/116; 29/874
See application file for complete search history.

(56) References Cited

U.S. PATENT DOCUMENTS

| | | | |
|---|---|---|---|
| 3,328,372 A | 6/1967 | Thomas et al. | |
| 3,427,366 A | 2/1969 | Verdol et al. | |
| 3,642,964 A | 2/1972 | Rausch, Jr. et al. | |
| 4,043,331 A | 8/1977 | Martin et al. | |
| 4,103,079 A | 7/1978 | Thaler | |
| 4,276,394 A | 6/1981 | Kennedy et al. | |
| 4,316,973 A | 2/1982 | Kennedy | |
| 4,342,849 A | 8/1982 | Kennedy | |
| 4,423,185 A | 12/1983 | Matsumoto et al. | |
| 4,477,604 A | 10/1984 | Oechsle, III | |
| 4,486,572 A | 12/1984 | Kennedy | |
| 4,570,270 A | 2/1986 | Oechsle, III | |
| 4,675,361 A | 6/1987 | Ward, Jr. et al. | |

(Continued)

FOREIGN PATENT DOCUMENTS

| | | |
|---|---|---|
| BR | 9003841 | 2/1992 |
| CA | 2278680 | 8/1998 |

(Continued)

OTHER PUBLICATIONS

Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).

(Continued)

*Primary Examiner* — Niketa Patel
*Assistant Examiner* — Alyssa M Alter
(74) *Attorney, Agent, or Firm* — Faegre Baker Daniels LLP

(57) ABSTRACT

The present invention is directed to a medical electrical lead including an insulative lead body formed, at least in part, from a polyisobutylene urethane, urea or urethane/urea copolymer. In some applications, the lead body can include at least one outer tubular insulator and/or an inner elongated member formed from a polyisobutylene urethane, urea or urethane/urea copolymer. Portions of the lead body formed form the polyisobutylene urethane, urea or urethane/urea copolymer can be either extruded or molded.

26 Claims, 21 Drawing Sheets

(56) References Cited

U.S. PATENT DOCUMENTS

| | | |
|---|---|---|
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward, Jr. |
| 4,880,883 A | 11/1989 | Grasel et al. |
| 4,888,389 A | 12/1989 | Kennedy et al. |
| 4,906,673 A | 3/1990 | Mori et al. |
| 4,939,184 A | 7/1990 | Kennedy |
| 5,017,664 A | 5/1991 | Grasel et al. |
| 5,120,813 A | 6/1992 | Ward, Jr. et al. |
| 5,149,739 A | 9/1992 | Lee |
| 5,194,505 A | 3/1993 | Brugel |
| 5,212,248 A | 5/1993 | Knoll et al. |
| 5,332,791 A | 7/1994 | Knoll et al. |
| 5,340,881 A | 8/1994 | Kennedy et al. |
| 5,428,123 A | 6/1995 | Ward et al. |
| 5,442,010 A | 8/1995 | Hauenstein |
| 5,442,015 A | 8/1995 | Kennedy et al. |
| 5,589,563 A | 12/1996 | Ward et al. |
| 5,637,647 A | 6/1997 | Faust |
| 5,663,234 A | 9/1997 | Kennedy et al. |
| 5,677,386 A | 10/1997 | Faust |
| 5,741,331 A | 4/1998 | Pinchuk |
| 5,852,118 A | 12/1998 | Horrion et al. |
| 5,874,484 A | 2/1999 | Dirckx et al. |
| 6,005,051 A | 12/1999 | Kennedy et al. |
| 6,010,715 A | 1/2000 | Wick et al. |
| 6,072,003 A | 6/2000 | Horrion et al. |
| 6,093,197 A | 7/2000 | Bakula et al. |
| 6,200,589 B1 | 3/2001 | Kennedy et al. |
| 6,228,945 B1 | 5/2001 | Kennedy et al. |
| 6,365,674 B1 | 4/2002 | Kaufhold et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 | 9/2003 | Meijs et al. |
| 6,849,667 B2 | 2/2005 | Haseyama et al. |
| 6,870,024 B2 | 3/2005 | Haubennestel et al. |
| 7,101,956 B2 | 9/2006 | Benz et al. |
| 7,105,622 B2 | 9/2006 | Kennedy et al. |
| 7,196,142 B2 | 3/2007 | Kennedy et al. |
| 7,292,890 B2 | 11/2007 | Whitehurst et al. |
| 7,347,751 B2 | 3/2008 | Sweeney et al. |
| 7,715,922 B1 | 5/2010 | Tan |
| 2003/0125499 A1 | 7/2003 | Benz et al. |
| 2003/0204022 A1 | 10/2003 | Kennedy et al. |
| 2004/0054210 A1 | 3/2004 | Benz et al. |
| 2004/0198901 A1 | 10/2004 | Graham et al. |
| 2005/0031874 A1 | 2/2005 | Michal et al. |
| 2005/0060022 A1 | 3/2005 | Felt et al. |
| 2005/0288476 A1 | 12/2005 | Yilgor et al. |
| 2006/0047083 A1 | 3/2006 | Yilgor et al. |
| 2006/0223946 A1 | 10/2006 | Faust et al. |
| 2006/0264577 A1 | 11/2006 | Faust et al. |
| 2007/0051531 A1 | 3/2007 | Borganonkar et al. |
| 2007/0093604 A1 | 4/2007 | Kennedy |
| 2007/0203302 A1 | 8/2007 | Kennedy et al. |
| 2007/0282411 A1* | 12/2007 | Franz et al. ............ 607/116 |
| 2008/0167423 A1 | 7/2008 | Richards et al. |
| 2009/0187162 A1* | 7/2009 | Ohara et al. ............ 604/523 |
| 2009/0326077 A1 | 12/2009 | Desai et al. |
| 2010/0023104 A1 | 1/2010 | Smith |
| 2010/0069578 A1 | 3/2010 | Faust |
| 2010/0075018 A1 | 3/2010 | Desai et al. |
| 2010/0107967 A1 | 5/2010 | Yanaka et al. |
| 2010/0179298 A1 | 7/2010 | Faust |
| 2010/0241208 A1 | 9/2010 | Pinchuk |
| 2011/0054580 A1 | 3/2011 | Desai et al. |
| 2012/0077934 A1 | 3/2012 | Faust et al. |
| 2013/0079487 A1 | 3/2013 | Faust et al. |

FOREIGN PATENT DOCUMENTS

| | | |
|---|---|---|
| CN | 1248606 | 3/2000 |
| DE | 19610350 | 9/1997 |
| EP | 0259492 | 3/1988 |
| EP | 0610714 | 8/1994 |
| EP | 0837097 | 8/1999 |
| EP | 1061092 | 12/2000 |
| EP | 0961796 | 5/2002 |
| EP | 0732349 | 7/2002 |
| EP | 1489109 | 12/2004 |
| JP | 11-131325 | 5/1999 |
| JP | 11131325 A | 5/1999 |
| JP | 2008-238761 | 10/2008 |
| WO | WO 87/04625 | 8/1987 |
| WO | WO 93/22360 | 11/1993 |
| WO | WO 95/26993 | 10/1995 |
| WO | WO 97/00293 | 1/1997 |
| WO | WO 97/47664 | 12/1997 |
| WO | WO 98/33832 | 8/1998 |
| WO | WO 03/042273 | 5/2003 |
| WO | WO 2004/014453 | 2/2004 |
| WO | WO 2004/044012 | 5/2004 |
| WO | WO 2004/113400 | 12/2004 |
| WO | WO 2006/110647 | 10/2006 |
| WO | 2007117566 | 10/2007 |
| WO | WO 2008/060333 | 5/2008 |
| WO | WO 2008/066914 | 6/2008 |
| WO | WO 2008/112190 | 9/2008 |
| WO | WO 2008/127730 | 10/2008 |
| WO | WO 2008/156806 | 12/2008 |
| WO | WO 2009/058397 | 5/2009 |
| WO | WO 2009/158600 | 12/2009 |
| WO | WO 2009/158609 | 12/2009 |
| WO | 2010039986 | 4/2010 |
| WO | WO 2010/081132 | 7/2010 |
| WO | 2010111280 | 9/2010 |
| WO | WO2011060161 A1 | 9/2010 |
| WO | WO2011022583 A1 | 2/2011 |

OTHER PUBLICATIONS

International Search Report and Written Opinion issued in PCT/US2010/028334, Dated May 6, 2010, 12 pages.

Office Action issued in U.S. Appl. No. 11/400,059, mailed Aug. 24, 2010.

Santos, R. et al., "New Telechelic Polymers and Sequential Copolymers by Polyfunctional Initiator-Transfer-Agents (Inifers)", Polymer Bulletin, 11:341-348 (1984).

Wohlfarth, C., "Permittivity (Dielectric Constant) of Liquids", CRC Handbook, 91st ed. 2010-2011, p. 6-186 to 6-207.

Non-Final Office Action issued in U.S. Appl. No. 11/400,059, mailed Apr. 11, 2011.

Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).

Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).

Kang, Jungmee et al., "Rendering Polyureas Melt Processible", Journal of Polymer Science Part A: Polymer Chemistry, vol. 49, 2461-2467 (2011).

Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).

International Search Report and Written Opinion issued in PCT/US2010/047633, Jun. 17, 2011, 12 pages.

International Search Report and Written Opinion issued in PCT/US2010/047703, mailed Jun. 17, 2011, 12 pages.

Ako, Masayuke et al., "Polyisobutylene-based urethane foams I. Comparative reactivities of hydroxyl-terminated polyisobutylene-diols and -triols and other hydroxyl-capped polyols with isocyanate", Polymer Bulletin 19(2), 137-143 (1988).

(56) References Cited

OTHER PUBLICATIONS

Ako, Masayuke et al., "Polyisobutylene-based urethane foams II. Synthesis and properties of novel polyisobutylene-based flexible polyurethane foams", Journal of Applied Polymer Science, vol. 37(5), Feb. 5, 1989, pp. 1351-1361.
Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.
Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).
Cozzens, David et al., "Long term in vitro biostability of segmented polyisobutylene-based thermoplastic polyurethanes", Journal of Biomedicals Materials Research Journal, 2010, pp. 1-9.
De, Priyadarsi et al., "Carbocationic Polymerization of Isobutylene Using Methylaluminum Bromide Coinitiators: Synthesis of Bromoally Functional Polyisobutylene" Macromolecules, Oct. 2006, 39(2), 7527-7533.
De, Priyadarsi et al., "Relative Reactivity of C4 Olefins toward the Polyisobutylene Cation" Macromolecules 2006, 39, 6861-6870.
Gadkari A. et al., "Preparation and biocompatibility of Novel Polar-Nonpolar Networks. Osynthesis, Characterization and Histological-Bacterial Analysis Of Mixed Polytetrahydrofuran-Polyisobutylene Networks", Polymer Bulletin, vol. 22, No. 1, Jul. 1, 1989, pp. 25-32.
Giusti, Paolo et al., "Synthesis and Characterization of New potentially Hemocompatible Thermoplastic Elastomers", p. 371, Abstract, 1986.
Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.
Higashihara, T. et al., "Synthesis of Poly(isobutylene-block-methyl methacrylate) by a Novel Coupling Approach", Macromolecules, 39:5275-5279 (2006).
Ioffe, David et al., "Bromine, Organic Compounds", Kirk-Othmer Encyclopedia of Chemical Technology, vol. 4, pp. 340-365, © 2002.
Ivan, B. et al., "Synthesis of New Polyisobutylene-Based Polyurethanes", Am. Chem. Soc., Div. Org. Coat. Plast. Prepr., 43, 908-913 (1980).
Jenny, C. et al., "A New Insulation Material for Cardiac Leads with Potential for Improved performance", HRS 2005, HeartRhythm, 2, S318-S319 (2005).
Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).
Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).
Kennedy, J.P. et al., "Designed Polymers by Carbocationic Macromolecular Engineering: Theory and practice", Hanser Publishers 1991, pp. 191-193 and 226-233.
Kennedy, J.P. et al., "Polyisobutylene-Based Diols and Polyurethanes", Urethane Chemistry and Applications, Ed., K.H. Edwards, ACS Symp. Book Series, 172, Washington, D.C. 1981, pp. 383-391.
Kennedy, J.P. et al., "Polyisobutylene-Based Diols and Polyurethanes" Advances in Urethane Science and Technology, vol. 8, 1981, pp. 245-251.
Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.
Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.
Kennedy, Joseph P. "Synthesis, Characterization and Properties of Polyisobutylene-Based Polyurethanes", 6th International Technical/Marketing Conference: Polyurethane—New Paths to Progress—Marketing—Technology, Journal of Cellular Plastics, 1983, 19:288-307.
Kennedy, Joseph P. "Synthesis, Characterization and Properties of Polyisobutylene-Based Polyurethanes", Journal of Elastomers and Plastics, vol. 17 (Jan. 1985), pp. 82-88.
Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.
Kennedy, Joseph P., "Polyurethanes Based on Polyisobutylenes", Chemtech, Nov. 1986, 16(11), pp. 694-697.
Lelah, M.D. et al., "Polyurethanes in Medicine", CRC Press, Boca Raton, FL 1986, Chapter 3.
Li, J. et al., "Polyisobutylene supports—a non-polar hydrocarbon analog of PEG supports", Tetrahedron, 61(51):12081-12092, Dec. 2005.
Macias, A. et al., "Preparacion y reticulacion de poliisobutilenos de bajo peso molecular con grupos terminales reactivos", Revista de Plasticos Modernos, Num 332 (Apr. '83), pp. 412-418.
Miller, J. A., "New Directions in Polyurethane Research", Organic Coatings and Applied Polymer Science Proceedings, vol. 47, Copyright 1982 by ACS, pp. 124-129.
Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).
Mitzner, E., "Modification of segmented poly(ether urethanes) by incorporation of Poly(isobutylene)glycol", J.M.S.—Pure Appl. Chem., A34(1), pp. 165-178 (1997).
Miyabayashi, Toshio et al., "Characterization of Polyisobutylene-Based Model Urethane Networks", Journal of Applied Polymer Science, vol. 31, pp. 2523-2532 (1986).
Muller, J.P. et al., "Surface modification of polyurethanes by multicomponent polyaddition reaction", Journal of Materials Science Letters 17(2), 1998, pp. 115-118.
Ojha et al., "Synthesis and Characterization of Thermoplastic Polyurethaneureas based on Polyisobutylene and Poly(tetramethylene oxide) Segments", J. Macromolecular Science, Part A, vol. 47(3), pp. 186-191, Mar. 2010.
Ojha, Umaprasana et al., "Syntheses and characterization of novel biostable polyisobutylene based thermoplastic polyurethanes", Polymer 50(2009), 3448-3457.
Ojha, Umaprasana et al., "Synthesis and Characterization of Endfunctionalized Polyisobutylenes for Sharpless-type Click Reactions", Polymer Preprints 2007, 48(2), 786.
Puskas, J.E. et al., "polyisobutylene-based biomaterials", Journal of Polymer Science Part A: Polymer Chemistry, vol. 42, Issue 13 (2004) pp. 3091-3109.
Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48(2), 233-234.
Ranade, S. et al., "Physical characterization of controlled release of paclitaxel from the TAXUS™ Express2™ drug-eluting stent", Journal of Biomedical Materials Research Part A, 71A (2004) 625-634.
Ranade, S.V. et al., Styrenic Block copolymers for Biomaterial and Drug Delivery Applications, Acta Biomater. Jan. 2005; 1(1): 137-44.
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Speckhard, T.A. et al., "New generation polyurethanes", Polymer News 1984, 9(12), 354-358.
Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.
Speckhard, T.A. et al., "Properties of Polyisobutylene Polyurethane Block Copolymers: 3. hard segments based on 4,4'-dicyclohexylmethane diisocyanate (H12MDI) and butane diol", Polymer, vol. 26, No. 1, Jan. 1985, pp. 70-78.

(56) References Cited

OTHER PUBLICATIONS

Speckhard, T.A. et al., "Properties of Polyisobutylene-Polyurethane Block Copolymers", Journal of Elastomers and Plastics, vol. 15 (Jul. 1983), pp. 183-192.

Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No. 6, pp. 337-349.

Speckhard, T.A. et al., "Ultimate Tensite Properties of Segmented Polyurethane Elastomers", Rubber Chem. Technol., 59, 405-431 (1986).

Tonelli, C. et al., "New Fluoro-Modified Thermoplastic Polyurethanes" Journal of Applied Polymer Science, vol. 87, Issue 14 (2003) 2279-2294.

Virmani, R. et al. Circulation Feb. 17, 2004, 109)6) 701-5.

Wang, F. Polydimethylsiloxane Modification of Segmented Thermoplastic Polyurethanes and Polyureas, PhD. Dissertation, Virginia Polytechnic Institute and State university, Apr. 13, 1998.

Weisberg, David M. et al., "Synthesis and Characterization of Amphiphilic Poly(urethaneurea)-comb-polyisobutylene Copolymers", Macromolecules 2000, 33(12), pp. 4380-4389.

Weissmuller, M. et al., "Preparation and end-linking of hydroxyl-terminated polystyrene star macromolecules", Macromolecular Chemistry and Physics 200(3), 1999, 541-551.

Wiggins, Michael J. et al., "Effect of soft-segment chemistry on polyurethane biostability during in vitro fatigue loading", Journal of biomedical materials research, 68(4), 2004, 668-683.

Wu, Yuguang et al., "The role of adsorbed fibrinogen in platelet adhesion to polyurethane surfaces: A comparison of surface hydrophobicity, protein adsorption, monoclonal antibody binding, and platelet adhesion", Journal of Biomedical Materials Research, Part A, Sep. 15, 2005, vol. 74A, No. 4, pp. 722-738.

Xu, Ruijian et al., "Low permeability biomedical polyurethane nanocomposites", Journal of Miomedical Materials Resarch, 2003, vol. 64A, pp. 114-119.

Yang, M. et al., J. biomed. Mater. Res. 48 (1999) 13-23.

Yeh, J. et al., "Moisture diffusivity of Biomer® versus Biomer®-coated Polyisobutylene polyurethane urea (PIB-PUU): a potential blood sac material for the artificial heart", Journal of Materials Science Letters 13(19), 1994, pp. 1390-1391.

Yoon, Sung C. et al., "Surface and bulk structure of segmented poly(ether urethanes) with Perfluoro Chain Extenders. 5. Incorporation of Poly(dimethylsiloxane) and Polyisobutylene Macroglycols", Macromolecules Mar. 14, 1994, 27(6), pp. 1548-1554.

International Search Report issued in PCT/US2009/048845, mailed Oct. 6, 2009, 3 pages.

International Search Report issued in PCT/US2009/048827, mailed Oct. 6, 2009, 3 pages.

International Search Report and Written Opinion issued in PCT/US2007/008528, dated Oct. 2, 2007.

International Search Report and Written Opinion issued in PCT/US2006/013308, dated Aug. 25, 2006.

International Search Report and Written Opinion issued in PCT/US2007/012948, dated Nov. 28, 2007.

International Search Report issued in PCT/US2010/020733, mailed May 6, 2010.

Faust, R. et al., "Method to Prepare Block Copolymers by the Combination of Cationic and Anionic Polymerization", U.S. Appl. No. 12/225,905, filed Apr. 5, 2007.

Tan, J. et al., "In Vivo Biostability Study of A New Lead Insulation Material," Cardiostim 2006, Europace Supplements, 8, 179PW/9 (2006).

Wright, James I., "Using Polyurethanes in Medical Applications", 5 pages. Downloaded from http://www.cmdm.com on Oct. 17, 2006.

\* cited by examiner

MEDICAL DEVICES INCLUDING POLYISOBUTYLENE BASED POLYMERS AND DERIVATIVES THEREOF

CROSS-REFERENCE TO RELATED APPLICATION

This application claims the benefit under 35 U.S.C. §119 of U.S. Provisional Application No. 61/239,115, filed on Sep. 2, 2009, entitled "MEDICAL DEVICES INCLUDING POLYISOBUTYLENE BASED POLYMERS AND DERIVATIVES THEREOF," which is herein incorporated by reference in its entirety for all purposes. Additionally, this application is a continuation-in-part of U.S. application Ser. No. 12/784,559, filed on May 21, 2010, entitled "POLYISOBUTYLENE URETHANE, UREA AND URETHANE/UREA COPOLYMERS AND MEDICAL LEADS CONTAINING THE SAME," which claims the benefit under 35 U.S.C. §119 of U.S. Provisional Application No. 61/239,115, filed on Sep. 2, 2009, entitled "MEDICAL DEVICES INCLUDING POLYISOBUTYLENE BASED POLYMERS AND DERIVATIVES THEREOF," both of which are herein incorporated by reference in their entirety for all purposes.

FIELD OF THE INVENTION

The present invention relates to medical electrical leads, and more specifically to medical electrical leads and lead components incorporating polyisobutylene based urethane, urea and urethane/urea copolymers and their derivatives.

BACKGROUND OF THE INVENTION

Polymeric materials such as silicone rubber, polyurethane, and other polymers are used as insulation materials for medical electrical leads. For cardiac rhythm management systems, such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles.

During and after implantation, the leads and lead body materials are exposed to various external conditions imposed, for example, by the human muscular, skeletal and cardiovascular systems, body fluids, the pulse generator, other leads, and surgical instruments used during implantation and explanation procedures. Accordingly, there are ongoing efforts to identify lead body materials that are able to withstand a variety of conditions over a prolonged period of time while maintaining desirable flexibility characteristics and a minimized profile.

SUMMARY OF THE INVENTION

A first example provides an implantable medical lead comprising an elongated lead body comprising a lumen, at least one conductor disposed within the lumen and at least one electrode operatively coupled to the conductor and disposed along the lead body, wherein the lead body has a shore hardness ranging from about 30A to about 75D and comprises a polyisobutylene urethane, urea or urethane/urea copolymer comprising soft polymer segments and hard polymer segments. The soft polymer segments comprise a polyisobutylene segment and at least one additional polymer segment comprising a residue of a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol. A weight ratio of soft segments to hard segments in the copolymer ranges from 50:50 to 90:10.

A second example is an implantable medical lead according to example 1, wherein a weight ratio of polyisobutylene to additional polymer ranges from about 70:30 to about 90:10.

A third example is an implantable medical lead according to any of the foregoing examples, wherein the soft segments comprise a polyisobutylene segment and a residue of a polyether diol.

A fourth example is an implantable medical lead according to any of the foregoing examples wherein the soft segments comprise a polyisobutylene segment and a residue of a polytetramethylene oxide diol A fifth example is an implantable medical lead according to any of the foregoing examples, wherein a weight ratio of polyisobutylene to polytetramethylene oxide ranges from about 70:30 to about 90:10.

A sixth example is an implantable medical lead according to any of the foregoing examples, wherein the polyisobutylene segment comprises a residue of an unsaturated polyisobutylene diol.

A seventh example is an implantable medical lead according to any of the foregoing examples wherein the lead body comprises an inner lumen and an inner surface of the lumen comprises the copolymer.

An eighth example is an implantable medical lead according to any of the foregoing examples, wherein the conductor is a coiled conductor having a co-radial configuration and wherein the inner surface is disposed over an outer surface of the coiled conductor.

A ninth example is an implantable medical lead according to any of the foregoing examples, wherein the lead body comprises an inner tubular layer and an outer tubular layer, wherein at least one of the inner and outer tubular layers comprises a polyisobutylene urethane, urea or urethane/urea copolymer.

A tenth example is an implantable medical lead according to any of the foregoing examples, wherein the lead comprises first and second coiled conductors having a co-axial configuration, wherein the inner tubular layer is disposed between the first and the second conductors, and wherein the outer tubular layer is disposed over the second coiled conductor.

An eleventh example is an implantable medical lead comprising an elongated lead body comprising a lumen, at least one conductor disposed within the lumen and at least one electrode operatively coupled to the conductor and disposed along the lead body, wherein the lead body comprises a polyisobutylene urethane, urea or urethane/urea copolymer in each of a proximal region comprising a first shore hardness, a middle region comprising a second shore hardness and a distal region comprising a third shore hardness. The copolymer comprises soft polymer segments and hard polymer segments and wherein the soft polymer segments comprise a residue of a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol.

A twelve example is an implantable medical lead according to any of the foregoing claims, wherein the distal region comprises a shore hardness ranging from about 30A to about 70A.

A thirteenth example is an implantable medical lead according to any of the foregoing claims, wherein the middle region comprises a shore hardness ranging from about 60A to about 85A.

A fourteenth example is an implantable medical lead according to any of the foregoing claims, wherein the proximal region comprises a shore hardness ranging from about 85A to about 100A.

A fifteenth example is an implantable medical lead according to any of the foregoing claims, wherein soft segment in each region comprises a residue of a polytetramethylene oxide diol.

A sixteenth example is an implantable medical lead according to any of the foregoing claims, wherein a weight ratio of polyisobutylene to polytetramethylene in each region ranges from about 70:30 to about 90:10.

A seventeenth example is an implantable medical lead according to any of the foregoing claims, wherein a weight ratio of soft segments to hard segments in the copolymer in each region ranges from 50:50 to 90:10.

An eighteenth example is an implantable medical lead according to any of the foregoing claims, wherein the proximal region comprises a first weight ratio of soft segments to hard segments in the polyisobutylene urethane, urea or urethane/urea copolymer, the middle region comprises a second weight ratio of soft segments to hard segments in the polyisobutylene urethane, urea or urethane/urea copolymer, and the distal region comprises a third weight ratio of soft segments to hard segments in the polyisobutylene urethane, urea or urethane/urea copolymer.

A nineteenth example is an implantable medical lead comprising a flexible, elongated lead body comprising an inner tubular member including at least one longitudinal lumen therethrough; at least one conductor extending through the at least one lumen of the inner tubular member, the conductor including an electrode having an exposed surface relative to the lead body; and at least one polymeric component connected to at least one of the lead body, conductor and electrode, the at least one polymeric component comprising a polyisobutylene urethane, urea or urethane/urea copolymer. The copolymer comprises soft polymer segments and hard polymer segments and the soft polymer segments comprise a polyisobutylene segment and at least one additional polymer segment comprising a residue of a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol.

A twentieth example is an implantable medical lead according to any of the foregoing claims, wherein the at least one polymeric component comprises a lead terminal, terminal pin, a lead tip, O-ring, seal or a header.

A twenty-first example is an implantable medical lead according to any of the foregoing claims, wherein the at least one polymeric component comprises a thin film disposed on or adjacent to the exposed surface of the electrode.

A twenty-second example is an implantable medical lead according to any of the foregoing claims, wherein the thin film comprises a plurality of electrospun fibers comprising the polyisobutylene urethane, urea or urethane/urea copolymer.

A twenty-third example is an implantable medical lead according to any of the foregoing claims, wherein the at least one polymeric layer comprises a polymer tube disposed adjacent to the exposed surface of the electrode.

A twenty-fourth example is a method of manufacturing an implantable medical lead comprising forming a lead body portion having a shore hardness ranging from about 30A to about 75D from a polymer material comprising a polyisobutylene urethane, urea or urethane/urea copolymer, wherein the copolymer comprises soft polymer segments and hard polymer segments in a weight ratio of from 50:50 to 90:10. The soft polymer segments comprise a polyisobutylene segment and at least one additional polymer segment comprising a residue of a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol. The lead body portion is associated with a conductor and an electrode connected to the conductor.

A twenty-fifth example is an implantable medical lead according to any of the foregoing examples wherein the lead body portion is formed by extruding the polymer material.

A twenty-sixth example is an implantable medical lead according to any of the foregoing examples, wherein the polyisobutylene urethane, urea or urethane/urea copolymer comprises an unsaturated polyisobutylene segment.

A twenty-seventh example is an implantable medical lead according to any of the foregoing examples, wherein the polyisobutylene urethane, urea or urethane/urea copolymer comprises a polyisobutylene segment formed from a saturated polyisobutylene diol having a number average molecular weight of between about 1000 and 5000.

A twenty-eighth example is an implantable medical lead according to any of the foregoing examples, wherein the polyisobutylene urethane, urea or urethane/urea copolymer comprises a polytetramethylene oxide segment formed from a polytetramethylene oxide diol having a number average molecular weight of between about 500 and 3000.

A twenty-ninth example is an implantable medical lead according to any of the foregoing examples, further comprising the step of combining the polyisobutylene urethane, urea or urethane/urea copolymer with at least one processing aid, antioxidant or wax to form a mixture.

A thirtieth example is an implantable medical lead according to any of the foregoing examples, further comprising the step of extruding the lead body portion from the mixture.

A thirty-first example is an implantable medical lead according to any of the foregoing examples, wherein forming the lead body portion comprises forming a proximal region including a first shore hardness, a middle region comprising a second shore hardness and a distal region comprising a third shore hardness, wherein each of the first, second and third regions comprises the polyisobutylene urethane, urea or urethane/urea copolymer.

A thirty-second example is an implantable medical lead according to any of the foregoing examples, wherein the proximal region comprises a first weight ratio of soft segments to hard segments in the polyisobutylene urethane, urea or urethane/urea copolymer, the middle region comprises a second weight ratio of soft segments to hard segments in the polyisobutylene urethane, urea or urethane/urea copolymer, and the distal region comprises a third weight ratio of soft segments to hard segments in the polyisobutylene urethane, urea or urethane/urea copolymer.

A thirty-third example is an implantable medical lead according to any of the foregoing examples, wherein the forming step comprises electrospinning the polyisobutylene urethane, urea or urethane/urea copolymer.

A thirty-fourth example is a method for forming a medical electrical lead having coiled electrode including a polymeric layer, the method comprising electrospinning multiple fibers comprising a polyisobutylene urethane, urea or urethane/urea copolymer; and depositing the fibers onto at least a portion of the coiled electrode to form the polymeric layer.

A thirty-fifth example is an implantable medical lead according to any of the foregoing examples, further comprising the step of electrospinning the fibers directly onto the coiled electrode.

A thirty-sixth example is an implantable medical lead according to any of the foregoing examples, further comprising the step of electrospinning the fibers onto a substrate to form a fibrous thin film and wrapping multiple layers of the fibrous thin film over the coiled electrode.

A thirty-seventh example is an implantable medical lead according to any of the foregoing examples, medical electrical lead according to claim 534, wherein the proximal region comprises a durometer ranging from about 85A to about 70A, the middle region comprises a durometer ranging from about 60A to about 85A, and the distal region comprises a durometer ranging from about 30A to about 70A.

These and other aspects and embodiments as well as various advantages of the present invention will become readily apparent to those of ordinary skill in the art upon review of the Detailed Description and any Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

In accordance with various aspects of the invention, implantable and insertable medical devices are provided, which include one or more polymeric regions containing one or more polyisobutylene urethane, urea or urethane/urea copolymers (also referred to herein collectively as "polyisobutylene urethane copolymers"). As used herein, a "polymeric region" is a region (e.g., an entire device, an insulative layer, a device component, a device coating layer, etc.) that contains polymers, for example, from 50 wt % or less to 75 wt % to 90 wt % to 95 wt % to 97.5 wt % to 99 wt % or more polymers.

Medical electrical devices of the present invention typically include (a) an electronic signal generating component and (b) one or more leads. The electronic signal generating component commonly contains a source of electrical power (e.g., a sealed battery) and an electronic circuitry package, which produces electrical signals that are sent into the body (e.g., the heart, nervous system, etc.). Leads comprise at least one flexible elongated conductive member (e.g., a wire, cable, etc.), which is insulated along at least a portion of its length, generally by an elongated polymeric component often referred to as a lead body. The conductive member is adapted to place the electronic signal generating component of the device in electrical communication with one or more electrodes, which provide for electrical connection with the body. Leads are thus able to conduct electrical signals to the body from the electronic signal generating component. Leads may also relay signals from the body to the electronic signal generating component.

Examples of medical electrical devices of the present invention include, for example, implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

Figure 1:
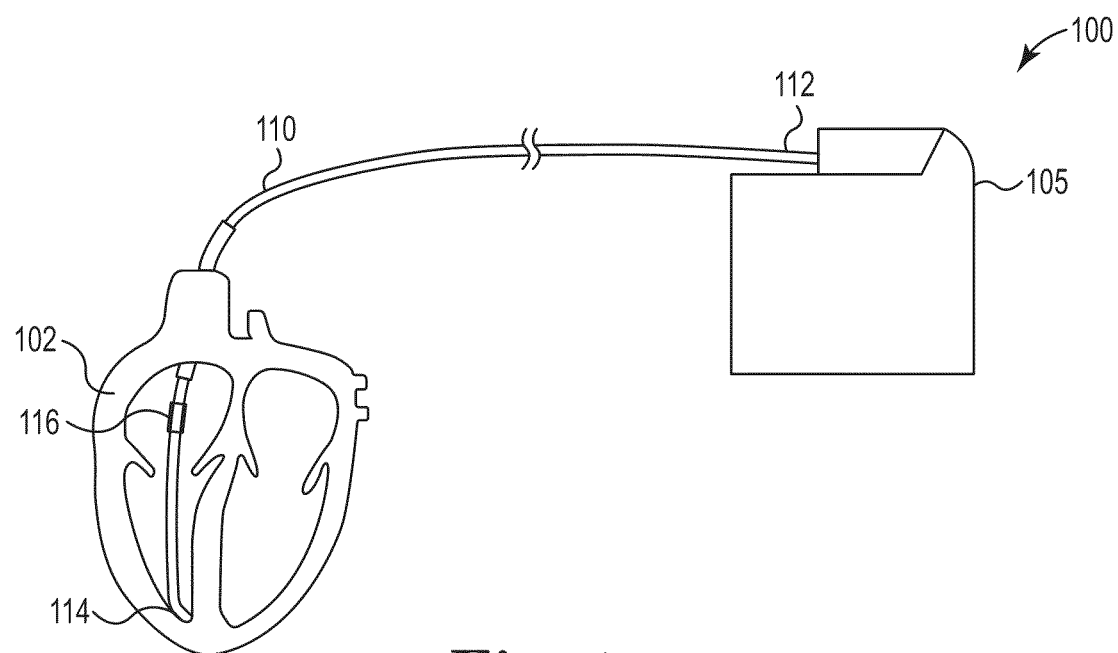
FIG. 1 is a schematic illustration of an implantable cardiac device including a lead shown implanted in a sectional view of a heart.

FIG. 1 is a schematic illustration of a lead system 100 for delivering and/or receiving electrical pulses or signals to stimulate, shock, and/or sense the heart 102. The system 100 includes a pulse generator 105 and a lead 110. The pulse generator 105 includes a source of power as well as an electronic circuitry portion. The pulse generator 105 is a battery-powered device which generates a series of timed electrical discharges or pulses. The pulse generator 105 is generally implanted into a subcutaneous pocket made in the wall of the chest. Alternatively, the pulse generator 105 may be placed in a subcutaneous pocket made in the abdomen, or in another location. It should be noted that while the lead 110 is illustrated for use with a heart, the lead 110 is suitable for other forms of electrical stimulation/sensing as well. For example, the lead 110 can be used for neurostimulation. Examples of neurostimulation leads and instruments for their implantation are reported in, e.g., U.S. Pat. No. 7,292,890 to Whitehurst et al., U.S. Pat. No. 6,600,956 to Maschino et al., and U.S. Pat. No. 6,093,197 to Bakula et al, which are hereby incorporated by reference.

The lead 110 extends from a proximal end 112, where it is coupled with the pulse generator 105 to a distal end 114, which is coupled with a portion of a heart 102, when implanted or otherwise coupled therewith. An outer insulating lead body extends generally from the proximal end 112 to the distal end 114 of the lead 110. Also disposed along a portion of the lead 110, for example near the distal end 114 of the lead 110, is at least one electrode 116 which electrically couples the lead 110 with the heart 102. At least one electrical conductor (not shown) is disposed within the lead body and extends generally from the proximal end 112 to the distal end 114 of the lead 110. The at least one electrical conductor electrically couples the electrode 116 with the proximal end 112 of the lead 110. The electrical conductor carries electrical current and pulses between the pulse generator 105 and the electrode 116, and to and from the heart 102. In one option, the at least one electrical conductor is a coiled conductor. In another option, the at least one electrical conductor includes one or more cables. Typical lengths for such leads vary from about 35 cm to 40 cm to 50 cm to 60 cm to 70 cm to 80 cm to 90 cm to 100 cm to 110 cm to 120 cm, among other values. Typical lead diameters vary from 4 to 5 to 6 to 7 to 8 to 9 French, among other values.

As noted above, portions of the medical electrical devices of the present invention are formed from or contain polyisobutylene urethane copolymers as further described herein. These polyisobutylene urethane copolymers may be used to form a variety of polymeric components for medical electrical devices (e.g., pacemakers, defibrillators, heart failure devices, neurostimulation devices, etc.) including portions of the lead body through which at least one conductor extends, such as single-lumen and multi-lumen extrusions and inner and outer tubular (tube-shaped) insulation layers, as well as lead tip materials, headers, and various other lead components (e.g., seal O-rings, etc.).

The polyisobutylene urethane copolymers described herein may also be used as encapsulation/insulation materials for electronic signal generating/sensing components, examples of which include implantable pulse generators, implantable cardioverter-defibrillators (ICDs) and implantable cardiac resynchronization therapy (CRT) devices. Such electronic signal generating/sensing components may be used, for example, in conjunction with right ventricular lead systems, right atrial lead systems, and left atrial/ventricular lead systems and may be used to treat, for example, bradycardia, tachycardia (e.g., ventricular tachycardia) or cardiac dyssynchrony in a vertebrate subject (including humans, pets and livestock). As previously noted, the present invention is also applicable to leads and electronic signal generating/sensing components for neurostimulation systems such as spinal cord stimulation (SCS) systems, deep brain stimulation (DBS) systems, peripheral nerve stimulation (PNS) systems, gastric nerve stimulation systems, cochlear implant systems, retinal implant systems, and pain management systems, among others.

As is well known, "polymers" are molecules containing multiple copies (e.g., from 5 to 10 to 25 to 50 to 100 to 250 to 500 to 1000 or more copies) of one or more constitutional units, commonly referred to as monomers. As used herein, the term "monomers" may refer to free monomers and to those that have been incorporated into polymers, with the distinction being clear from the context in which the term is used.

Polymers may take on a number of configurations including linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit (i.e., a monomer). "Copolymers" are polymers that contain multiple copies of at least two dissimilar constitutional units.

Polyurethanes are a family of copolymers that are synthesized from polyfunctional isocyanates (e.g., diisocyanates, including both aliphatic and aromatic diisocyanates) and polyols (e.g., macroglycols). Commonly employed macroglycols include polyester diols, polyether diols and polycarbonate diols that form polymeric segments of the polyurethane. Typically, aliphatic or aromatic diols or diamines are also employed as chain extenders, for example, to impart improved physical properties to the polyurethane. Where diamines are employed as chain extenders, urea linkages are formed and the resulting polymers may be referred to as polyurethane/polyureas.

Polyureas are a family of copolymers that are synthesized from polyfunctional isocyanates and polyamines, for example, diamines such as polyester diamines, polyether diamines, polysiloxane diamines, polyhydrocarbon diamines and polycarbonate diamines. As with polyurethanes, aliphatic or aromatic diols or diamines may be employed as chain extenders.

According to certain aspects of the invention, the polyisobutylene urethane copolymer includes (a) one or more polyisobutylene segments, (b) one or more additional polymeric segments (other than polyisobutylene segments), (c) one or more segments that includes one or more diisocyanate residues, and optionally (d) one or more chain extenders. Examples of such copolymers and methods for their synthesis are generally described in WO 2008/060333, WO 2008/066914 and U.S. application Ser. No. 12/492,483 filed on Jun. 26, 2009 entitled POLYISOBUTYLENE URETHANE, UREA AND URETHANE/UREA COPOLYMERS AND MEDICAL DEVICES CONTAINING THE SAME, all of which are incorporated herein by reference in their entirety.

As used herein, a "polymeric segment" or "segment" is a portion of a polymer. Segments can be unbranched or branched. Segments can contain a single type of constitutional unit (also referred to herein as "homopolymeric segments") or multiple types of constitutional units (also referred to herein as "copolymeric segments") which may be present, for example, in a random, statistical, gradient, or periodic (e.g., alternating) distribution.

The polyisobutylene segments of the polyisobutylene urethane copolymers are generally considered to constitute soft segments, while the segments containing the diisocyanate residues are generally considered to constitute hard segments. The additional polymeric segments may include soft or hard polymeric segments. As used herein, soft and hard segments are relative terms to describe the properties of polymer materials containing such segments. Without limiting the foregoing, a soft segment may display a Tg that is below body temperature, more typically from 35° C. to 20° C. to 0° C. to −25° C. to −50° C. or below. A hard segment may display a Tg that is above body temperature, more typically from 40° C. to 50° C. to 75° C. to 100° C. or above. Tg can be measured by differential scanning calorimetry (DSC), dynamic mechanical analysis (DMA) and thermomechanical analysis (TMA).

Suitable soft segments include linear, branched or cyclic polyalkyl, polyalkene and polyalkenyl segments, polyether segments, fluoropolymer segments including fluorinated polyether segments, polyester segments, poly(acrylate) segments, poly(methacrylate) segments, polysiloxane segments and polycarbonate segments.

Examples of suitable polyether segments include linear, branched and cyclic homopoly(alkylene oxide) and copoly(alkylene oxide) segments, including homopolymeric and copolymeric segments formed from one or more, among others, methylene oxide, dimethylene oxide (ethylene oxide), trimethylene oxide, propylene oxide, tetramethylene oxide, pentamethylene oxide, hexamethylene oxide, octamethylene oxide and decamethylene oxide.

Examples of suitable fluoropolymer segments include perfluoroacrylate segments and fluorinated polyether segments, for example, linear, branched and cyclic homopoly(fluorinated alkylene oxide) and copoly(fluorinated alkylene oxide) segments, including homopolymeric and copolymeric segments formed from one or more of, among others, perfluoromethylene oxide, perfluorodimethylene oxide (perfluoroethylene oxide), perfluorotrimethylene oxide and perfluoropropylene oxide.

Examples of suitable polyester segments include linear, branched and cyclic homopolymeric and copolymeric segments formed from one or more of, among others, alkyleneadipates including ethyleneadipate, propyleneadipate, tetramethyleneadipate, and hexamethyleneadipate.

Examples of suitable poly(acrylate) segments include linear, branched and cyclic homopoly(acrylate) and copoly(acrylate) segments, including homopolymeric and copolymeric segments formed from one or more of, among others, alkyl acrylates such as methyl acrylate, ethyl acrylate, propyl acrylate, isopropyl acrylate, butyl acrylate, sec-butyl acrylate, isobutyl acrylate, 2-ethylhexyl acrylate and dodecyl acrylate.

Examples of suitable poly(methacrylate) segments include linear, branched and cyclic homopoly(methacrylate) and copoly(methacrylate) segments, including homopolymeric and copolymeric segments formed from one or more of, among others, alkyl methacrylates such as hexyl methacrylate, 2-ethylhexyl methacrylate, octyl methacrylate, dodecyl methacrylate and octadecyl methacrylate.

Examples of suitable polysiloxane segments include linear, branched and cyclic homopolysiloxane and copolysiloxane segments, including homopolymeric and copolymeric segments formed from one or more of, among others, dimethyl siloxane, diethyl siloxane, and methylethyl siloxane.

Examples of suitable polycarbonate segments include those comprising one or more types of carbonate units,

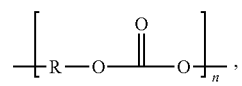

where R may be selected from linear, branched and cyclic alkyl groups. Specific examples include homopolymeric and copolymeric segments formed from one or more of, among others, ethylene carbonate, propylene carbonate, and hexamethylene carbonate.

Examples of hard polymeric segments include various poly(vinyl aromatic) segments, poly(alkyl acrylate) and poly(alkyl methacrylate) segments.

Examples of suitable poly(vinyl aromatic) segments include linear, branched and cyclic homopoly(vinyl aromatic) and copoly(vinyl aromatic) segments, including homopolymeric and copolymeric segments formed from one or more vinyl aromatic monomers including, among others, styrene, 2-vinyl naphthalene, alpha-methyl styrene, p-methoxystyrene, p-acetoxystyrene, 2-methylstyrene, 3-methylstyrene and 4-methylstyrene.

Examples of suitable poly(alkyl acrylate) segments include linear, branched and cyclic homopoly(alkyl acrylate) and copoly(alkyl acrylate) segments, including homopolymeric and copolymeric segments formed from one or more acrylate monomers including, among others, tert-butyl acrylate, hexyl acrylate and isobornyl acrylate.

Examples of suitable poly(alkyl methacrylate) segments include linear, branched and cyclic homopoly(alkyl methacrylate) and copoly(alkyl methacrylate) segments, including homopolymeric and copolymeric segments formed from one or more alkyl methacrylate monomers including, among others, methyl methacrylate, ethyl methacrylate, isopropyl methacrylate, isobutyl methacrylate, t-butyl methacrylate, and cyclohexyl methacrylate.

Particularly suitable polyisobutylene urethane copolymers include (a) a polyisobutylene soft segment, (b) a polyether soft segment, (c) a hard segment containing diisocyanate residues, (d) optional chain extenders as further described below and/or (e) optional end capping materials as further described below.

The weight ratio of soft segments to hard segments in the polyisobutylene urethane copolymers of the present invention can be varied to achieve a wide range of physical and mechanical properties, including Shore hardness, and to achieve an array of desirable functional performance. For example, the weight ratio of soft segments to hard segments in the polymer can be varied from 99:1 to 95:5 to 90:10 to 75:25 to 50:50 to 25:75 to 10:90 to 5:95 to 1:99, more particularly from 95:5 to 90:10 to 80:20 to 70:30 to 65:35 to 60:40 to 50:50, and even more particularly, from about 80:20 to about 50:50.

The shore hardness of the polyisobutylene urethane copolymers of embodiments of the present invention can be varied by controlling the weight ratio of soft segments to hard segments. Suitable short hardness ranges include for example, from 45A, more particularly from 50A to 52.5A to 55A to 57.5A to 60A to 62.5A to 65A to 67.5A to 70A to 72.5A to 75A to 77.5A to 80A to 82.5A to 85A to 87.5A to 90A to 92.5A to 95A to 97.5A to 100A. In one embodiment, a polyisobutylene urethane copolymer with a soft segment to hard segment weight ratio of 80:20 results in a Shore Hardness of about 60-71A, a polyisobutylene urethane copolymer having a soft segment to hard segment weight ratio of 65:35 results in a Shore hardness of 80-83A, a polyisobutylene urethane copolymer having a soft segment to hard segment weight ratio of 60:40 result in a Shore hardness 95-99A, and a polyisobutylene urethane copolymer having a soft segment to hard segment weight ratio of 50:50 result in a Shore hardness >100A. Higher hardness materials (e.g., 55 D and above up to 75 D) can also be prepared by increasing the ratio of hard to soft segments. Such harder materials may be particularly suitable for use in the PG header device, tip and pin areas of leads and headers of neuromodulation cans.

The polyisobutylene and additional polymeric segments can vary widely in molecular weight, but typically are composed of between 2 and 100 repeat units (monomer units), among other values, and can be incorporated into the polyisobutylene polyurethane copolymers of the invention in the form of polyol (e.g., diols, triols, etc.) or polyamine (e.g., diamines, triamines, etc.) starting materials. Although the discussion to follow is generally based on the use of polyols, analogous methods may be performed and analogous compositions may be created using polyamines and polyol/polyamine combinations.

Suitable polyisobutylene polyol starting materials include linear polyisobutylene diols and branched (three-arm) polyisobutylene triols. More specific examples include linear polyisobutylenediols with a terminal —OH functional group at each end. Further examples of polyisobutylene polyols include poly(styrene-co-isobutylene) diols and poly(styrene-b-isobutylene-b-styrene) diols which may be formed, for example, using methods analogous to those described in See, e.g., J. P. Kennedy et al., "Designed Polymers by Carbocationic Macromolecular Engineering: Theory and Practice," Hanser Publishers 1991, pp. 191-193, Joseph P. Kennedy, *Journal of Elastomers and Plastics* 1985 17: 82-88, and the references cited therein. The polyisobutylene diol starting materials can be formed from a variety of initiators as known in the art. In one embodiment, the polyisobutylene diol starting material is a saturated polyisobutylene diol that is devoid of C=C bonds.

Examples of suitable polyether polyol starting materials include polytetramethylene oxide diols and polyhexamethylene diols, which are available from various sources including Sigma-Aldrich Co., Saint Louis, Mo., USA and E.I. duPont de Nemours and Co., Wilmington, Del., USA. Examples of polysiloxane polyol starting materials include polydimethylsiloxane diols, available from various sources including Dow Corning Corp., Midland Mich., USA, Chisso Corp., Tokyo, Japan. Examples of suitable polycarbonate polyol starting materials include polyhexamethylene carbonate diols such as those available from Sigma-Aldrich Co. Examples of polyfluoroalkylene oxide diol starting materials include ZDOLTX, Ausimont, Bussi, Italy, a copolyperfluoroalkylene oxide diol containing a random distribution of —$CF_2CF_2O$— and —$CF_2O$— units, end-capped by ethoxylated units, i.e., $H(OCH_2CH_2)_nOCH_2CF_2O(CF_2CF_2O)_p(CF_2O)_qCF_2CH_2O(CH_2CH_2O)_nH$, where n, p and q are integers. Suitable polystyrene diol starting materials (α,ω-dihydroxy-terminated polystyrene) of varying molecular weight are available from Polymer Source, Inc., Montreal, Canada. Polystyrene diols and three-arm triols may be formed, for example, using procedures analogous to those described in M. Weißmüller et al., "Preparation and end-linking of hydroxyl-terminated polystyrene star macromolecules," *Macromolecular Chemistry and Physics* 200(3), 1999, 541-551.

In some embodiments, polyols (e.g., diols, triols, etc.) are synthesized as block copolymer polyols. Examples of such block copolymer polyols include poly(tetramethylene oxide-b-isobutylene) diol, poly(tetramethylene oxide-b-isobutylene-b-tetramethylene oxide) diol, poly(dimethyl siloxane-b-isobutylene) diol, poly(dimethyl siloxane-b-isobutylene-b-dimethyl siloxane) diol, poly(hexamethylene carbonate-b-isobutylene) diol, poly(hexamethylene carbonate-b-isobutylene-b-hexamethylene carbonate) diol, poly(methyl methacrylate-b-isobutylene) diol, poly(methyl methacrylate-b-isobutylene-b-methyl methacrylate) diol, poly(styrene-b-isobutylene) diol and poly(styrene-b-isobutylene-b-styrene) diol (SIBS diol).

Diisocyanates for use in forming the urethane copolymers of the invention include aromatic and non-aromatic (e.g., aliphatic) diisocyanates. Aromatic diisocyanates may be selected from suitable members of the following, among others: 4,4'-methylenediphenyl diisocyanate (MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate, 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI).

In a particular embodiment, a polyether diol such as polytetramethylene oxide diol (PTMO diol), polyhexameethylene oxide diol (PHMO diol), polyoctamethylene oxide diol or polydecamethylene oxide diol is combined with the polyisobutylene diol and diisocyanate to form a polyisobutylene polyurethane copolymer with generally uniform distribution of the polyurethane hard segments, polyisobutylene segments and polyether segments to achieve favorable micro-phase separation in the polymer. The polyether segments may also improve key mechanical properties such as Shore hardness, tensile strength, tensile modulus, flexural modulus, elongation, tear strength, flex fatigue, tensile creep, and abrasion performance, among others.

The polyisobutylene urethane copolymers in accordance with the invention may further include one or more optional chain extender residues and/or end groups. Chain extenders can increase the hard segment length (or, stated another way, can increase the ratio of hard segment material to soft segment material in the urethane, urea or urethane/urea polymer), which can in turn result in a polymer with higher modulus, lower elongation at break and increased strength. For instance the molar ratio of soft segment to chain extender to diisocyanate (SS:CE:DI) can range, for example, from 1:9:10 to 2:8:10 to 3:7:10 to 4:6:10 to 5:5:10 to 6:4:10 to 7:3:10 to 8:2:10 to 9:1:10.

Chain extenders are typically formed from aliphatic or aromatic diols (in which case a urethane bond is formed upon reaction with an isocyanate group) or aliphatic or aromatic diamines (in which case a urea bond is formed upon reaction with an isocyanate group). Chain extenders may be selected from suitable members of the following, among others: alpha, omega-alkane diols such as ethylene glycol (1,2-ethane diol), 1,4-butanediol, 1,6-hexanediol, alpha,omega-alkane diamines such as ethylene diamine, dibutylamine (1,4-butane diamine) and 1,6-hexanediamine, or 4,4'-methylene bis(2-chloroaniline). Chain extenders may be also selected from suitable members of, among others, short chain diol polymers (e.g., alpha,omega-dihydroxy-terminated polymers having a molecular weight less than or equal to 1000) based on hard and soft polymeric segments (more typically soft polymeric segments) such as those described above, including short chain polyisobutylene diols, short chain polyether polyols such as polytetramethylene oxide diols, short chain polysiloxane diols such as polydimethylsiloxane diols, short chain polycarbonate diols such as polyhexamethylene carbonate diols, short chain poly(fluorinated ether) diols, short chain polyester diols, short chain polyacrylate diols, short chain polymethacrylate diols, and short chain poly(vinyl aromatic) diols.

In certain embodiments, the biostability and/or biocompatibility of the polyisobutylene urethane copolymers in accordance with the invention may be improved by end-capping the copolymers with short aliphatic chains (e.g., $[-CH_2]_n-CH_3$ groups, $[-CH_2]_n-C(CH_3)_3$ groups, $[-CH_2]_n-CF_3$ groups, $[-CH_2]_n-C(CF_3)_3$ groups, $[-CH_2]_n-CH_2OH$ groups, $[-CH_2]_n-C(OH)_3$ groups and $[-CH_2]_n-C_6H_5$ groups, etc., where n may range, for example, from 1 to 2 to 5 to 10 to 15 to 20, among others values) that can migrate to the polymer surface and self assemble irrespective of synthetic process to elicit desirable immunogenic response when implanted in vivo. Alternatively, a block copolymer or block terpolymer with short aliphatic chains (e.g., $[-CH_2]_n$-b-$[-CH_2O]_n-CH_3$ groups, $[-CH_2]_n$-b-$[-CH_2O]_n-CH_2CH_2C(CH_3)_3$ groups, $[-CH_2]_n$-b-$[-CH_2O]_n-CH_2CH_2CF_3$ groups, $[-CH_2]_n$-b-$[CH_2O]_n-CH_2CH_2C(CF_3)_3$ groups, $[-CH_3]_n$-b-$[-CH_2O]_n-CH_2CH_2OH$ groups, $[-CH_2]_n$-b-$[-CH_2O]_n-C(OH)_3$ groups, $[-CH_2]_n$-b-$[-CH_2O]_n-CH_2CH_2-C_6H_5$ groups, etc., where n may range, for example, from 1 to 2 to 5 to 10 to 15 to 20, among others values) that can migrate to the surface and self assemble can be blended with the copolymer toward the end of synthesis. These end-capping segments may also help to improve the thermal processing of the polymer by acting as processing aids or lubricants. Processing aids, antioxidants, waxes and the like may also be separately added to aid in thermal processing.

Various techniques may be employed to synthesize the polyisobutylene urethane copolymers from the diol and diisocyanate starting materials. The reaction may be conducted, for example, in organic solvents or using supercritical $CO_2$ as a solvent. Ionomers can be used for polymer precipitation.

In certain other embodiments, a one step method may be employed in which a first macrodiol (M1) (e.g., a polymeric diol such as an unsaturated or a saturated polyisobutylene diol,), a second macrodiol (M2) (e.g., a polyether diol) and a diisocyante (DI) (e.g., MDI, TDI, etc.) are reacted in a single step. Molar ratio of diisocyanate relative to the first and second diols is 1:1. For example, the ratio DI:M1:M2 may equal 2:1:1, may equal 2:1.5:0.5, may equal 2:0.5:1.5, among many other possibilities. Where a ratio of DI:M1:M2 equal to 2:1:1 is employed, a polyurethane having the following structure may be formed -[DI-M1-DI-M2-]$_n$ although the chains are unlikely to be perfectly alternating as shown. In some embodiments, a chain extender is added to the reaction mixture, such that the molar ratio of diisocyanate relative to the first and second macrodiols and chain extender is 1:1. For example, the ratio DI:M1:M2:CE may equal 4:1:1:2, may equal 2:0.67:0.33:1, may equal 2:0.33:0.67:1, or may equal 5:1:1:3, among many other possibilities. Where a ratio of DI:M1:M2:CE equal to 4:1:1:2 is employed, a polyurethane having the following structure may be formed -[DI-M1-DI-CE-DI-M2-DI-CE-]$_n$, although the chains are unlikely to be perfectly alternating as shown.

In some embodiments, a two-step method is employed in which first and second macrodiols and diisocyante are reacted in a ratio of DI:M1:M2 of ≥2:1:1 in a first step to form isocyanate capped first and second macrodiols, for example DI-M1-DI and DI-M2-DI. In a second step, a chain extender is added which reacts with the isocyanate end caps of the macrodiols. In some embodiments, the number of moles of hydroxyl or amine groups of the chain extender may exceed the number of moles of isocyanate end caps for the macrodiols, in which case additional diisocyante may be added in the second step as needed to maintain a suitable overall stoichiometry. As above, the molar ratio of diisocyanate relative to the total of the first macrodiol, second macrodiol, and chain extender is typically 1:1, for example, DI:M1:M2:CE may equal 4:1:1:2, which may in theory yield an idealized polyurethane having the following repeat structure -[DI-M1-DI-CE-DI-M2-DI-CE-]$_n$, although the chains are unlikely to be perfectly alternating as shown. In other examples, the DI:M1:M2:CE ratio may equal 4:1.5:0.5:2 or may equal 5:1:1:3, among many other possibilities.

In some embodiments, three, four or more steps may be employed in which a first macrodiol and diisocyante are reacted in a first step to form isocyanate capped first macrodiol, typically in a DI:M1 ratio of ≥2:1 such that isocyanate end caps are formed at each end of the first macrodiol (although other ratios are possible including a DI:M1 ratio of 1:1, which would yield an average of one isocyanate end caps per macrodiol). This step is followed by second step in which the second macrodiol is added such that it reacts with one or both isocyanate end caps of the isocyanate capped first macrodiol. Depending on the relative ratios of DI, M1 and M2, this step may be used to create structures (among other statistical possibilities) such as M2-DI-M1-DI-M2 (for a DI:M1:M2 ratio of 2:1:2), M2-DI-M1-DI (for a DI:M1:M2 ratio of 2:1:1), or M1-DI-M2 (for a DI:M1:M2 ratio of 1:1:1).

In certain embodiments, a mixed macrodiol prepolymer, such as one of those in the prior paragraph, among others (e.g., M2-DI-M1-DI-M2, M1-DI-M2-DI-M1, DI-M1-DI-M2, etc.) is reacted simultaneously with a diol or diamine chain extender and a diisocyanate, as needed to maintain stoichiometry. For example, the chain extension process may be used to create idealized structures along the following lines, among others: -[DI-M2-DI-M1-DI-M2-DI-CE-]$_n$ or -[DI-M1-DI-M2-DI-CE-]$_n$, although it is again noted that the chains are not likely to be perfectly alternating as shown.

In certain other embodiments, a mixed macrodiol prepolymer is reacted with sufficient diisocyanate to form isocyanate end caps for the mixed macrodiol prepolymer (e.g., yielding DI-M2-DI-M1-DI-M2-DI, DI-M1-DI-M2-DI-M1-DI or DI-M1-DI-M2-DI, among other possibilities). This isocyanate-end-capped mixed macrodiol can then be reacted with a diol or diamine chain extender (and a diisocyanate, as needed to maintain stoichiometry). For example, the isocyanate-end-capped mixed macrodiol can be reacted with an equimolar amount of a chain extender to yield idealized structures of the following formulae, among others: -[DI-M2-DI-M1-DI-M2-DI-CE-]$_n$, -[DI-M1-DI-M2-DI-M1-DI-CE-]$_n$, or -[DI-M1-DI-M2-DI-CE-]$_n$.

As noted above, chain extenders can be employed to increase the ratio of hard segment material to soft segment material in the urethane, urea or urethane/urea polymers described herein, which can in turn result in a polymer with higher modulus, lower elongation at break and increased strength. For instance the molar ratio of soft segment to chain extender to diisocyanate (SS:CE:DI) can range, for example, from 1:9:10 to 2:8:10 to 3:7:10 to 4:6:10 to 5:5:10 to 6:4:10 to 7:3:10 to 8:2:10 to 9:1:10 to 10:0:10, among other values.

In a particular embodiment, the soft, segment of the polyisobutylene urethane copolymer is formed from a first soft macrodiol or macrodiamine (M1) and second soft macrodiol or macrodiamine (M2) in a molar ratio of M1 to M2 (M1:M2) from 99:1 to 95:5 to 90:10 to 75:25 to 66:33 to 50:50 to 25:75 to 10:90 to 5:95 to 1:99, more particularly, from 90:10 to 85:15 to 80:20 to 75:25 to 70:30 and most particularly from about 75:25 to about 50:50.

Exemplary number average molecular weights for M1 and M2 may range from 100 to 10000, more preferably 200 to 5000, most preferably 750 to 2500. Exemplary materials for M1 include polyisobutylene diols, whereas preferred materials for M2 include polyether diols such as polytetramethylene oxide (PTMO) diol and polyhexamethylene oxide (PHMO) diol. In one embodiment, M1 is polyisobutylene diol having a number average molecular weight between about 1000 and 5000 and M2 is PTMO having a number average molecular weight of about 900 and 1200.

The molar ratio and number average molecular weight of the diol starting materials may be used to calculate the weight ratio of first to second soft segments in the polyisobutylene urethane copolymer. For example, if 48.00 g polyisobutylene diol having a number average molecular weight of 1000 is reacted with 32.00 g PTMO having a number average molecular weight of 1000, the weight ratio polyisobutylene segment to PTMO segment would be 60:40. In embodiments in which the soft segments include polyisobutylene and polytetramethylene oxide, the resulting weight ratio ranges from 15:1 to 13:1 to 12:1 to 7.5:1 to 4.5:1 to 3:1 to 2:1 to 3:2 to 1:1 to 1:2 to 2:3, more particularly, from about 99:1 to 95:5 to 90:10 to 80:20 to 70:30.

In another embodiment, the ratio of PIB diol to polytetramethylene oxide diol included in the reaction mixture results in a polyisobutylene urethane copolymer having soft segments comprising no more than about 30 wt % polytetramethylene oxide, particularly between about 10 wt % and 30 wt % polytetramethylene oxide, more particularly between about 5 wt % and about 20 wt % polytetramethylene oxide and even more particularly between about 10 wt % and about 20 wt % polytetramethylene oxide based on the total weight of soft segment. The balance of the soft segment weight may comprise polyisobutylene.

In a further embodiment, the ratio of PIB diol to polyhexamethylene oxide diol included in the reaction mixture results in a polyisobutylene urethane copolymer having soft segments comprising no more than about 30 wt % polyhexamethylene oxide, particularly between about 10 wt % and 30 wt % polyhexamethylene oxide, more particularly between about 15 wt % and 25 wt % polyhexamethylene oxide and even more particularly between about 20 wt % and 25 wt % polyhexamethylene oxide based on the total weight of soft segment. The balance of the soft segment weight may comprise polyisobutylene.

Polyisobutylene urethane copolymers containing PTMO of no more than about 30% show minimal decrease in both weight and tensile strength and exhibit a continuous surface morphology when subjected to accelerated degradation testing indicating favorable biostability of these materials. Additionally, when the amount of polyether diol (e.g. PTMO) is increased, the degradation also increases, suggesting that a low PTMO content promotes biostability.

In yet another exemplary embodiment, the ratio of PIB diol to polyether diol (e.g., polytetramethylene oxide diol or polyhexamethylene diol) to polydimethylsiloxane diol included in the reaction mixture results in a polyisobutylene urethane, urea or urethane/urea copolymer having a weight ratio of polyisobutylene to polyether to polydimethylsiloxane ranging from about 60:20:20 to about 80:15:5.

Figure 2:
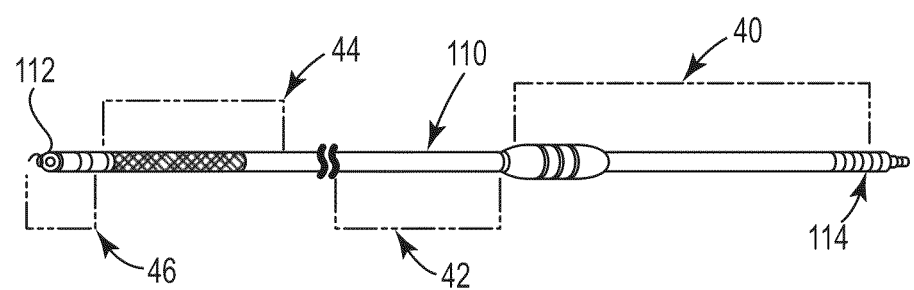
FIG. 2 is a perspective view of a medical electrical lead according to another embodiment of the present invention.

FIG. 2 illustrates a medical electrical lead including an elongated, insulative lead body 110 extending from a proximal end 112 to a distal end 114. According to various embodiments of the present invention, at least a portion of the lead body is manufactured from a polyisobutylene urethane copolymer as described above. In some embodiments, the polyisobutylene urethane copolymer can be extruded or molded into a portion or portions of the lead body. In other embodiments, the polyisobutylene urethane copolymer can be applied as a coating directly to the electrical conductors via a variety of techniques including, but not limited to spray coating, solution coating (dip coating), sputtering, plasma deposition and chemical vapor deposition, among others, to form at least a portion of the lead body. In still other embodiments, the polyisobutylene urethane copolymer can be molded over one or more portions of an existing lead body construction.

In embodiments in which the lead body 110 comprises the polyisobutylene urethane copolymer, the lead body may have a Shore hardness from about 30 A to about 75D and, more particularly, from about 30A to about 55D, even more particularly from about 50A to about 100A. The Shore Hardness may remain constant or vary along the length of the lead.

According to another embodiment, the lead body 110 has a Shore hardness that varies along its length. The Shore hardness of the lead body can be varied by utilizing different polyisobutylene urethane copolymer formulations to construct different portions of the lead body, by varying the composition of a selected polyisobutylene urethane copolymer along the length of the lead body during the manufacturing process and/or by blending different polyisobutylene urethane copolymers during manufacturing to achieve a desired Shore hardness in a selected portion of the lead body.

The lead body 110 shown in FIG. 2 includes multiple discrete regions, the approximate boundaries of which are illustrated by dashed lines. These regions include a proximal region 40, a middle region 42, a distal region 44 and a lead tip region 46. The proximal region 40 generally represents portions of the lead body 119 that reside in vessels somewhat distant from the heart. The middle region 42 represents portions of the lead body that reside in vessels that lead to the heart. The distal region 46 represents portions of the lead body that reside within the heart, and generally includes at least one of the electrodes 116. The lead tip region 46 generally represents the distal end of the lead body 110 which may include passive or active lead fixation member 36. The regions illustrated in FIG. 2 can vary in length and/or position on the lead body depending on the type and size of the medical electrical device 100, the intended treatment and/or the intended implantation procedure.

According to some embodiments of the present invention, the Shore hardness of each of at least regions 40, 42, and 44 differs. In one embodiment, the Shore hardness of the regions 40, 42, and 44 decreases along the length of the lead body 110 in a direction from the proximal end 112 to the distal end 114 of the lead body 110 such that the proximal region 40 has a Shore hardness that is greater than the Shore hardness of the distal region 44, and the middle region 42 has a Shore hardness that is less than the Shore hardness of the proximal region 40 and greater than the Shore hardness of the distal region 44. In one embodiment, the regions 40, 42, 44 form discrete regions of decreasing Shore hardness. In another embodiment, the Shore hardness can decrease gradually and continuously from the proximal region 40 to the tip region 44 of the lead body 110. In one embodiment the Shore hardness of the lead body is about 75D at the proximal region 40 of the lead body 110 and 45A the distal region 44 including the tip region 46 of the lead body 110. In further embodiments, the Shore hardness of the proximal region 40 ranges from about 85A to about 100A, the Shore hardness of the middle region 42 ranges from about 60A to about 85A and the Shore hardness of the distal region 46 ranges from about 30A to about 70A.

There are a number of approaches for varying the Shore hardness of the lead body along its length. In one embodiment, the Shore hardness of the polymeric material can be varied by extruding a lead body having a single unitary construction. In other embodiments, multiple segments can be separately formed and bonded together using, for example, heat and/or laser bonding/fusion and/or medical adhesive.

In some embodiments, a mix or volume ratio of the polymeric material used to form at least one portion (proximal 40 and/or middle 42) of the multi-lumen lead body 110 can be varied during an extrusion process. In this embodiment, polymeric materials having different durometers are blended together and then extruded to form the different portions of the lead body 110. In one embodiment, polyisobutylene polyurethane copolymer materials having different hard to soft segment ratios Shore hardness values can be blended together in different ratios and extruded to form the different portions of the lead body 110, having different Shore hardness values. In another embodiment, two or more polyisobutylene polyurethane copolymer materials having different soft and/or hard segments can be blended. In a further embodiment, a polyisobutylene polyurethane copolymer material can be blended with a different polymeric material to form one or more portions of the lead body 110.

During the extrusion process, a volume percent of a stiffer polymeric material (Polymer A) in the polymeric material blend changes from a maximum amount in the proximal portion 40 of the lead body to a minimum amount in the middle portion 42 of the lead body during extrusion of the lead body 110. Similarly, the volume percent of the softer polymeric material (Polymer B) in the polymeric blend changes from a minimum amount in the proximal portion 40 to a maximum amount in the middle portion of the lead body 110. In one embodiment, the durometer of Polymer A ranges from about 80A to about 100A, and the durometer of Polymer B ranges from about 25A to about 40A. In one embodiment, the volume ratio of Polymer A to Polymer B in the blend used to form proximal portion 40 of the lead body 110 ranges from about 75:25 to about 99:1. In one embodiment, the blend used to extrude the proximal portion 40 contains approximately 100% of Polymer A. In another embodiment, the volume ratio of Polymer A to Polymer B used to form a middle portion 42 of the lead body 110 ranges from about 35:65 to about 75:25.

In some embodiments, the distal portion and/or tip region of the multi-lumen lead body 110 can also be extruded and a mix or volume ratio of polymeric material used to form the distal and/or tip portions of the lead body 110 varied to vary the durometer in the distal and/or tip portions 44, 46 of the lead body 110.

In other embodiments, at least two lead body portions are separately manufactured (i.e., extruded or molded) and then connected to form the lead body 110. Connection can be achieved by overlapping the portions an applying an adhesive or by heat fusing to components with little or no overlapping portion.

Figure 3A:
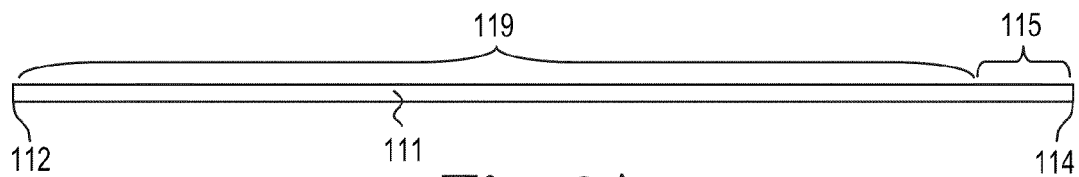
FIGS. 3A-3C are schematic illustrations of polymeric lead components, in accordance with three embodiments of the invention.

FIG. 3A is an illustration of a polymeric lead component 111 (e.g., an elongated tubular component, elongated multi-lumen extrusion, etc.) according to another embodiment having a proximal end 112 and a distal end 114. The polymeric lead component 111 contains an atraumatic tip portion 115 and a main lead portion 119, each of which may contain a polyisobutylene urethane copolymer. The atraumatic tip portion 115 may range, for example, from 1 to 2.5 to 5 to 12 cm in length, with the main lead portion 119 constituting the remainder of the length of the lead component 111 ranging from about 5 to 125 cm (from about 5 cm to 10 cm to 20 cm to 30 cm to 40 cm to 50 cm to 60 cm to 70 cm to 80 cm to 90 cm to 95 cm to 100 cm to 110 cm to 125 cm) in length, depending on lead type). The atraumatic tip portion 115 is relatively soft, having a Shore hardness ranging, for example, from 30A to 80A (e.g., from 30A to 40A to 50A to 52.5A to 55A to 57.5A to 60A to 62.5A to 65A to 67.5A to 70A to 72.5A to 75A to 77.5A to 80A). The main lead portion 119, on the other hand, is relatively hard to provide abrasion resistance and pushability, among other characteristics, having a Shore hardness ranging, for example, from 75A to 100A (e.g., from 75A to 85A to 90A to 92.5A to 95A to 97.5A to 100A).

More particularly the lead component 111 such as that shown in FIG. 3A may have a Shore hardness value of about 50A to 70A at a position that is 1 cm from the distal end (corresponding to a point within the atraumatic portion 115), and may have a Shore hardness value of about 90-A to 100A in the center of the lead component 111 (corresponding to a point within the main lead portion 119).

By providing portions with different Shore hardness values, optimized lead properties can be achieved. Generally, it is beneficial to have a relative harder main lead body and a relatively soft tip. The harder lead body provides for improved pushability and torque while the soft tip provide for improved maneuverability and lower pressure at the fixation site.

Figure 3B:

FIG. 3B also is an illustration of a polymeric lead component 111 (e.g., an elongated tubular component, elongated multi-lumen extrusion, etc.) having a proximal end 112 and a distal end 114. As with FIG. 3A, the polymeric lead component 111 of FIG. 3B includes an atraumatic tip portion 115 and a main lead portion 119. FIG. 3B further includes a proximal portion 117, which is designed, inter alia, to strike a balance between abrasion resistance and flexibility (e.g. for winding the lead into the pocket during implantation). The proximal portion 117 may range, for example, from 10 to 15 cm in length. The proximal portion 117 in this embodiment has a Shore hardness ranging from 80A to 98A (e.g., from 80A to 82.5A to 85A to 87.5A to 90A to 92.5A to 95A to 98A), and in certain embodiments, ranging from 80A to 90A (e.g., from 80A to 82.5A to 85A to 87.5A to 90A) for enhanced flexibility of the portion of the lead that extends from the implanted pacemaker can.

As a specific example a lead component 111 such as that illustrated in FIG. 3B may have a Shore hardness value of about 80A to 90A at a position that is 5 cm from the proximal end (corresponding to a point within the proximal portion 119), may have a Shore hardness value of about 50A to 70A at a position that is 1 cm from the distal end (corresponding to a point within the atraumatic tip portion 115), and a may have a Shore hardness value of about 90A to 100A at a position that is 10 cm from the distal end (corresponding to a point within the main lead portion 119).

Figure 3C:
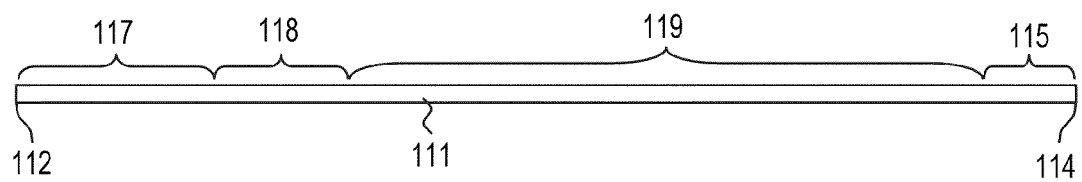

FIG. 3C is an illustration of a polymeric lead component 111 (e.g., an elongated tubular component, elongated multi-lumen extrusion, etc.) having a proximal end 112 and a distal end 114. As with FIG. 3B, the polymeric lead component 111 of FIG. 3C includes an atraumatic tip portion 115, a main lead portion 119, and a proximal portion 117. FIG. 3C further includes a suture sleeve portion 118, which is designed to provide clavicle/first rib crush resistance at the venous transition zone. The atraumatic tip portion 115 and the proximal portion 117 may have the above-described lengths and Shore hardness values. The suture sleeve portion 118 may range, for example, from 7.5 to 12 cm in length. The suture sleeve portion 118 in this embodiment has a Shore hardness ranging from 70A to 85A (e.g., from 70A to 72.5A to 75A to 77.5A to 80A to 82.5A to 85A), and in certain embodiments ranging from 70A to 80A (e.g., from 70A to 72.5A to 75A to 77.5A to 80A) for enhanced crush resistance. The main lead portion 119 in FIG. 3C may have the above Shore hardness values and may constitute the remainder of the lead component 111 length not taken up by the atraumatic tip portion 115, the proximal portion 117 and the suture sleeve portion 118 (e.g., the main lead portion 119 may range from about 10 cm to 20 cm to 30 cm to 40 cm to 50 cm to 60 cm to 70 cm to 80 cm in length, depending on lead type).

As a specific example a lead component 111 such as that shown in FIG. 3C may have a Shore hardness value of about 80A to 90A at a position that is 20 cm from the proximal end (corresponding to a point within the proximal portion 119), may have a Shore hardness value of about 70A-80A at a position that is 10 cm from the proximal end (corresponding to a point within the suture sleeve portion 118), may have a Shore hardness value of about 50A to 70A at a position that is 1 cm from the distal end (corresponding to a point within the atraumatic portion 115), and a may have a Shore hardness value of about 90A to 100 A at a position that is 10 cm from the distal end (corresponding to a point within the main lead portion 119).

In addition to optimizing the Shore hardness of portions of the polymeric lead component 111, the flexural modulus of these portions can also be optimized. In one embodiment, the main lead body portion 119 has a flexural modulus of about 4000 to 10,000 psi, the atraumatic tip portion has a flexural modulus of about 1000 to 5000 psi and the proximal portion 119 has a flexural modulus of about 4000 to 10,000 psi.

Each polymeric lead component 111 of FIGS. 3A-C may be formed from discrete polymeric components that correspond to portions 115, 117, 118 and 119. For example, such discrete components may be formed separately (e.g., by extrusion) and bonded to one another (e.g., by bonding with an adhesive, thermal fusion, etc.) to form the polymeric lead component 111. For example, discrete components corresponding to the atraumatic tip portion 115 and the main lead portion 119 may be bonded to one another to form the polymeric lead component 111 of FIG. 3A. As another example, discrete components corresponding to the atraumatic tip portion 115, the main lead portion 119 and the proximal portion 117 may be bonded to one another to form the polymeric lead component 111 of FIG. 33B. As yet another example, discrete components corresponding to the atraumatic tip portion 115, the main lead portion 119, the suture sleeve portion 118 and the proximal portion 117 may be bonded to one another to form the polymeric lead component 111 of FIG. 3C. The use of such discrete components can be used to form lead components 111 with abrupt transitions between the above described hardness ranges (i.e., transitions of 1 mm or less).

Alternatively, the polymeric composition may change continuously between the portions 115, 117, 118 and 119 of the polymeric lead component 111 (e.g., by forming a continuous tubular or multi-lumen extrusion in which the composition of the material being extruded is changed during the course of extrusion). In such embodiments, lead components 111 with gradual transitions between the above described hardness ranges (i.e., transitions of greater than 1 mm, more typically greater than 1 cm) may be formed.

If desired, each lead component 111 of FIGS. 3A-3C may be provided with a proximal terminal of high Shore hardness (not shown). For example such a proximal terminal may range from 2.5 to 5 cm in length and may range in Shore hardness from 60D to 70D to 80D to 90D, more preferably about 75D. Such a proximal terminal may be formed from a polyurethane with ratio of SS:HS between 60:40 to 30:70, more preferably between 60:40 to 45:55 and bonded to the lead component 111 (e.g., by thermoplastic bonding, by using a suitable adhesive, etc.).

Figure 4A:
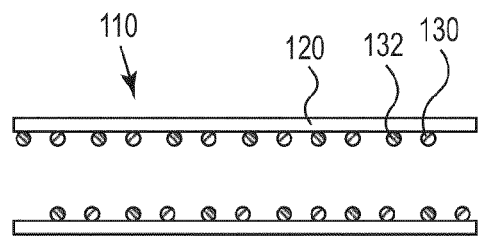
FIG. 4A is a schematic longitudinal cross sectional view of a portion of a medical lead, in accordance with an embodiment of the invention.

The polyisobutylene-based copolymers described herein may be employed in conjunction with various lead designs. For example, FIG. 4A is a schematic longitudinal cross sectional view of an insulated (non-electrode) portion of a medical lead 110 in accordance with the invention. The portion of the lead shown includes a first coiled conductor 130 and a second coiled conductor 132 disposed in a co-radial arrangement with one another. An advantage of a coiled configuration for the conductors 130, 132 is that the various types of movements experienced by the lead in vivo are converted into torsion, which the metals that are typically used to form the coils can readily tolerate. The coiled conductors 130, 132 may be made, for example, of stainless steel, Elgiloy, or MP35N, among other suitable conductive materials. The coiled conductors 130, 132 are disposed within a tubular insulation layer 120, which may be formed from polyisobutylene-based copolymers as described herein. The tubular insulation layer 120 acts to chemically, mechanically and electrically insulate the coiled conductors from the external environment and can also provide the lead with desirable mechanical characteristics such as flexibility, crush resistance, torqueability, and abrasion resistance, which characteristics may vary along the length of the layer 120. For example, the tubular insulation layer 120 may vary in Shore hardness along its length as described in any of FIGS. 3A-3C above, among other possibilities.

Such a tubular insulation layer 120 may be, for example, solvent coated over the coiled conductors 130,132, extruded over the coiled conductors 130,132, or first extruded and then disposed over the coiled conductors 130,132, among other possibilities. In the latter case, the pre-formed tubular insulation layer 120 may be bonded to insulating material provided on the coiled conductors 130, 132 (not shown) by a suitable elevated temperature process such as laser bonding (where the insulating material on the conductors is a thermoplastic material).

Figure 4B:
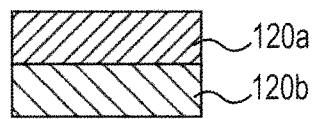
FIGS. 4B and 4C are alternative expanded views of a portion of FIG. 4A.

In another embodiment, the tubular insulation layer 120 can include two or more layers of polymeric material, which can form two or more coaxial tubular material regions as shown in FIG. 4B. The tubular insulation layer 120 includes two coaxial tubular material regions 120a and 120b. The two coaxial tubular material regions 120a and 120 can be formed from the same or different materials. For example, in one embodiment, the outer material region 120a can be formed from a polyisobutylene urethane copolymers such as described above according to the various embodiments and the inner material region 120b can be formed from a different material such as conventional polyurethanes, silicone rubbers, SIBS (styrene/isobutylene/styrene copolymers), and other polymers useful in lead body construction known to those of skill in the art. In another embodiment, both the inner and outer tubular material regions 120a and 120b can be formed from a polyisobutylene urethane copolymer such as described above according to the various embodiments.

In some embodiments, the outer material region 120a can be solvent coated over the inner material region 80b, co-extruded over the inner material region 120b, co-extruded with the inner material region 120b, or first extruded and then inserted over the inner material region 120b, among other possibilities. In some embodiments, the outer material region 120a can be fused to the inner material region 120b by a suitable elevated temperature process such as, for example, a laser bonding process or a thermal bonding process. The use of laser bonding can create the potential for high speed manufacturing of leads, reduced assembly time and/or improved production yield.

Figure 4C:
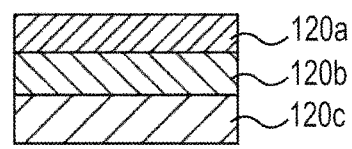
Figure 5:
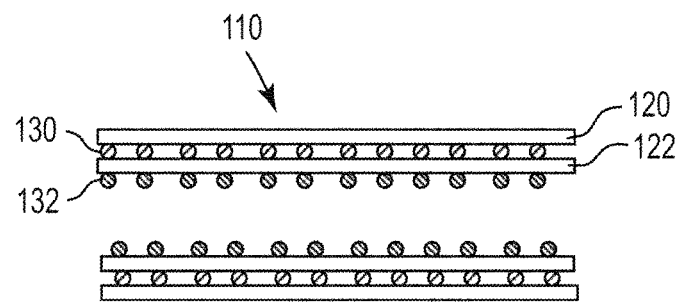
FIG. 5 is a schematic longitudinal cross sectional view of a portion of a medical lead, in accordance with yet another embodiment of the invention.

According to yet another embodiment, as shown in FIG. 4C, the lead body 110 can include three coaxial tubular material regions 120a, 120b and 120c. Each of the three co-axial tubular can be formed from the same or different materials. For example, in one embodiment, the inner and outer material regions 120a and 120c can be formed from, for example, a polyisobutylene urethane, urea or urethane/urea copolymer provided in accordance with the various embodiments of the present invention and the intervening region 120b can include a non-polyisobutylene urethane, urea or urethane/urea copolymer containing material. In another embodiment, only the outer material region 120 is formed from a polyisobutylene urethane, urea or urethane/urea copolymer-containing material.

Figure 6A:
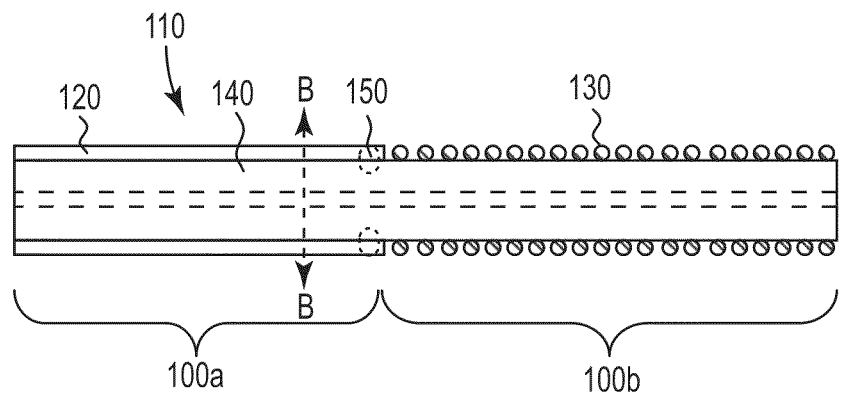
FIG. 6A is a schematic longitudinal cross sectional view of a portion of a medical lead, in accordance with another embodiment of the invention.
Figure 6B:
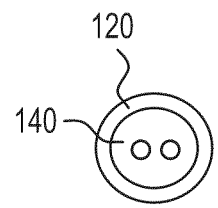
FIG. 6B is a cross section of the medical lead of FIG. 6A, taken along line B-B.

Like FIG. 4, FIG. 6 is a schematic longitudinal cross sectional view of an insulated portion of a medical lead 110 in accordance with the invention that includes first and second coiled conductors 130, 132. Unlike FIG. 4, the first and second coiled conductors 130,132 in FIG. 6 are disposed in a co-axial (rather than co-radial) arrangement with one another. An outer tubular insulation layer 120 is disposed over the outer coiled conductor 130. Like the tubular insulation layer of FIG. 4, the outer tubular insulation layer 120 of FIG. 6 may be formed from a polyisobutylene-based copolymer as described herein. The outer tubular insulation layer 120 may vary in Shore hardness along its length, for example, as described in FIGS. 3A-3C, among other possibilities. The inner coiled conductor 132 is provided with a further tubular insulation layer 122, which acts to insulate the coiled conductor 132 from the external environment (and from the outer coiled conductor 130 as well). The inner tubular insulation layer 122 may also be formed, for example, from a polyisobutylene urethane copolymer as described herein. Alternatively, a soft silicone material (e.g., 50A Shore hardness) may be used to form the inner tubular insulation layer 122 so as to have minimal impact on the mechanical properties of the lead.

The outer tubular insulation layer 120 of FIG. 6 can also comprise two or more material regions, for example, two or more layers of material, which may form two or more coaxial tubular material regions. Specific examples of two-material and three-material regions suitable for use in the outer tubular insulation layer 120 of FIG. 6 are described in conjunction with FIGS. 4B and 4C above.

Figure 7A:
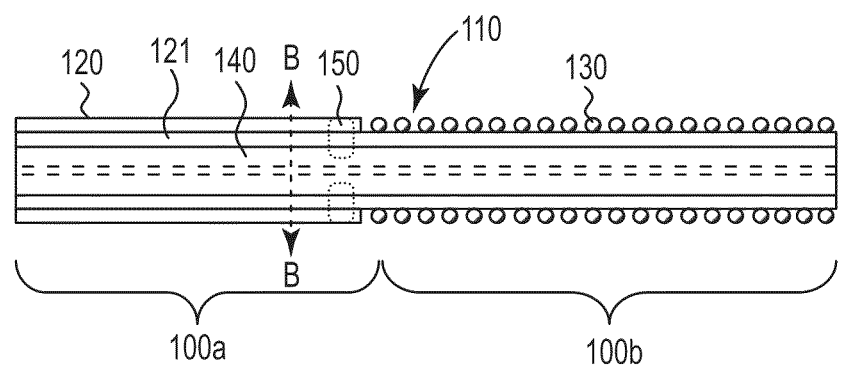
FIG. 7A is a schematic longitudinal cross sectional view of a portion of a medical lead, in accordance with another embodiment of the invention.

FIG. 7A is a schematic longitudinal cross sectional view illustrating an embodiment which includes an insulated (non-electrode) portion 100a and a non-insulated (electrode) portion 100b of a medical lead 110. The portion of the lead 110 shown includes a polymer-containing inner elongated member 140. Disposed over the right-hand portion 100b of the inner elongated member 140 is a coiled conductor 130 which may act, for example, as a shocking/defibrillation electrode for the medical lead 110. Because it acts as an electrode, the coiled conductor 130 is either uncoated or coated with a conductive layer (e.g., a layer of iridium oxide, etc.). Disposed over the left-hand portion 100a of the inner elongated member 140 is a tubular covering 120, which acts to smooth the transition between the non-electrode portion 100a and the electrode portion 100b (i.e., the tubular covering 120 is provided to create a continuous diameter for the device). For example, the thickness of the tubular covering 120 can be the same as the diameter of the conductor forming the coil 130, such that the maximum diameter of portion 100a matches that of portion 100b. (In addition to ensuring a smooth the transition between the electrode and non-electrode bearing portions 100b, 100a, the tubular covering 120 can also assist in insulating any conductor(s) lying within the inner elongated member 140, and may improve the mechanical characteristics of the lead.).

Figure 7B:
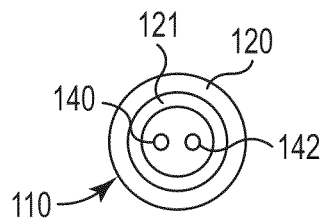
FIG. 7B is a cross section of the medical lead of FIG. 7A, taken along line B-B.

FIG. 7B is a cross section of the device of FIG. 7A, taken along line B-B, and shows a two-lumen inner elongated member 140 with outer tubular insulation layer 120. The lumens of the inner elongated member 140 may accommodate, for example, a guide wire and a conductor, two conductors, etc. Other configurations, including inner elongated members with one, four, five, six, seven, eight, etc. lumens are also possible.

The inner elongated member 140 of the device of FIGS. 7A-7B may be formed, for example, using a polyisobutylene-based copolymer as described herein. The inner elongated member 140 may vary in Shore hardness along its length, for example, as described in FIGS. 2A-2C, among other possibilities. An advantage associated with the use of polyisobutylene-based copolymers as described herein for forming inner elongated member 140 is that the member 140 can be extruded via a thermoplastic process. Similarly, the outer tubular insulation layer 120 may also be formed, for example, using a polyisobutylene-based copolymer as described herein. The outer tubular insulation layer 120 may also vary in Shore hardness along its length, for example, as described in FIGS. 2A-2C, among other possibilities. The outer tubular insulation layer 120 may be, for example, solvent coated over the inner elongated member 140, extruded over the inner elongated member 140, co-extruded with the inner elongated member 140, or first extruded and then inserted over the inner elongated member 140, among other possibilities.

An advantage associated with the use of polyisobutylene-based copolymers as described herein for forming both the outer tubular insulation layer 120 and the inner elongated member 140 is that the tubular insulation layer 120 can be fused to the inner elongated member 140 by a suitable elevated temperature process, for instance, a laser bonding process. Such a process may be used, for example, to create a ring-shaped thermally fused region 150 as shown in FIG. 4A (e.g., by rotating the device under laser irradiation). By extending the fused region entirely around the circumference of device, an effective seal is formed between the tubular insulation layer 120 and inner elongated member 140. Of course a laser bonding process can produce thermally fused regions of various shapes in addition to ring shaped regions. For example, the tubular covering 120 can be "spot-fused" to the inner elongated member 140 at various locations (in a process analogous to spot-welding) to prevent unacceptable levels of movement between the tubular covering 120 and inner elongated member 140 during implantation.

Figure 8:
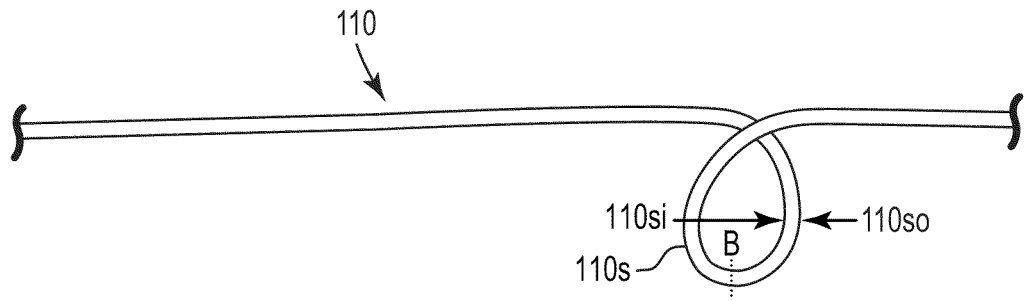
FIG. 8 is a partial schematic view of a portion of a medical lead in accordance with an embodiment of the invention.

FIG. 8 is a partial schematic view of a polymeric (non-electrode) portion of a medical lead 110 in accordance with the invention. The portion of the lead shown includes a single loop 110*s* of a spiral. Additional loops may be provided as desired. Typically, such a spiral will typically range from 1.5 to 5 cm in diameter.

Figure 9:
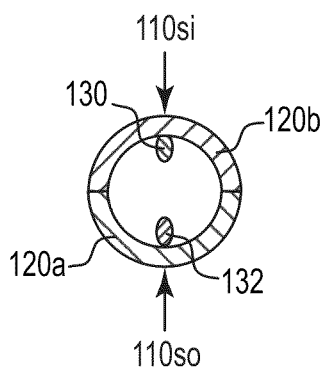
FIG. 9 is a cross section of the medical lead of FIG. 8, taken along line B-B.

FIG. 9 is an enlarged schematic cross-sectional view taken along line B-B of FIG. 6 and illustrates a first coiled conductor 130 and a second coiled conductor 132 disposed in a co-radial arrangement with one another (analogous to FIG. 4). The coiled conductors 130,132 are disposed within a tubular insulation structure, half of which is formed from a first material 120*a* and half of which is formed from a second material 120*b*. Each of the first and second materials 120*a*, 120*b* may be formed from polyisobutylene-based copolymers as described herein. The first material 120*a* corresponds to the surface 110*so* of the spiral 110*s* that faces radially outward from the spiral 110*s*. First material 120*a* is a relatively high hardness material, for example, one having a Shore hardness ranging from 90A to 95A to 100A. The second material 120*b* corresponds to the surface 110*si* of the spiral 110*s* that faces radially inward. Second material 120*b* is a relatively low hardness material, for example, one having a Shore hardness ranging from 50A to 60A to 70A to 80A to 90A to 100A.

Such a two-material lead insulation may be provided only in the area of the spiral 110*s*, or it may be provided along the entire length of the lead. The spiral 110*s* may correspond, for instance, to a portion of a left ventricular lead, or a heart failure lead that is to be positioned in the coronary sinus and may allow the lead to be passively fixed within the body. In such embodiments, the spiral will typically range from 2 to 5 cm in diameter and will be formed from the portion of the lead that lies between 1 and 10 cm from the distal end of the lead.

Figure 10:
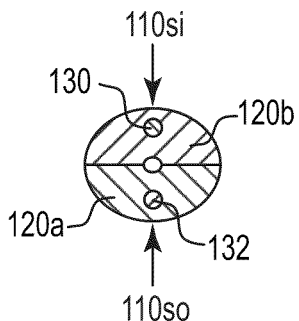
FIG. 10 is a cross section of the medical lead of FIG. 8, taken along line B-B, in an alternative embodiment to FIG. 9.

FIG. 10 is an alternative enlarged schematic cross-sectional view taken along line B-B of FIG. 8 and illustrates a first conductor 130 and a second conductor 132 disposed in two lumens of a multi-lumen elongated member, half of which is formed from a first material 120*a* and half of which is formed from a second material 120*b*, each of which may be formed from polyisobutylene-based copolymers as described herein. The first material 120*a* corresponds to the surface 110*so* of the spiral 110*s* that faces radially outward. Material 120*a* is a relatively high hardness material, for example, one having Shore hardness values like that of material 120*a* in FIG. 7. The second material 120*b* corresponds to the surface 110*si* of the spiral 110*s* that faces radially inward. Material 120*b* is relatively low hardness material, for example, one having Shore hardness values like that of material 120*b* in FIG. 9.

Material regions 120*a* and 120*b* in FIG. 9 and FIG. 10 or may be formed separately (e.g., by extrusion, molding, etc.) and bonded to one another (e.g., by thermoplastic bonding, by using a suitable adhesive, etc.). Alternatively, the material regions 120*a* and 120*b* may be simultaneously formed in a single extrusion operation.

The spiral of FIGS. 8-10 may be established, for example, by first mechanically forcing the lead 110 into a shape that includes the spiral 110*s*, then heating the lead to a suitable temperature (e.g., between the softening and melting temps of the materials 110*a* and 110*b*), followed by cooling the lead, thereby allowing the lead to memorize the coiled shape. For instance, the lead may be heated to between 140 and 200° C., depending on the composition of the lead, among other possibilities. In other embodiments, a spiral may be formed using molding techniques. A spiral may be established in vivo by disposing the lead over a relatively stiff guide wire which holds the lead in a substantially linear configuration. Upon removal of the guide wire the lead changes in shape in an effort to recover its memorized spiral shape.

Figure 11:
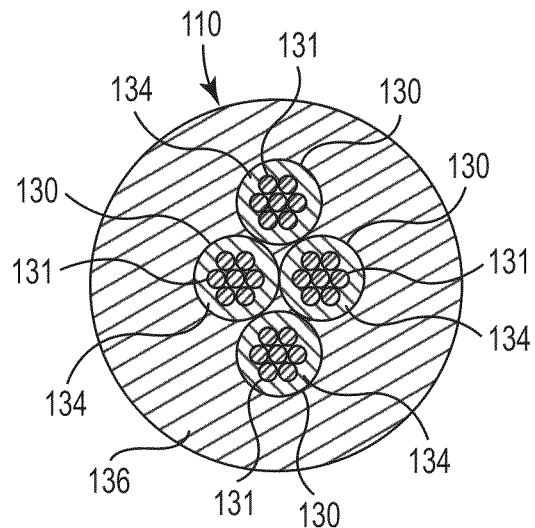
FIG. 11 is an end cross-sectional view of a portion of a medical electrical lead provided in accordance with another embodiment of the present invention.

FIG. 11 is an end cross-sectional view of the lead body 110 according to yet another embodiment of the present invention. As shown in FIG. 11, the insulative lead body 110 includes a plurality of cable conductors 130, each having a plurality of conductive filaments 131. The filaments 131 may be separately insulated from one another. According to one embodiment the cable conductors 130 can include at least one layer of insulation 134 provided over their outer periphery. In one embodiment, the outer tubular insulation 136 forming the lead body 110 can be co-extruded along with the cable conductors 130 or the individual filaments 131 forming the cable conductors 130. In another embodiment, the outer insulation 136 can be molded around the cable conductors 130. In one embodiment, the outer tubular insulation 136 can be formed from a polyisobutylene urethane copolymer such as described above according to the various embodiments. In a further embodiment, the insulation layer surrounding each of the individual cable conductors 130 also can be formed form a polyisobutylene urethane copolymer such as described above.

Figure 12A:
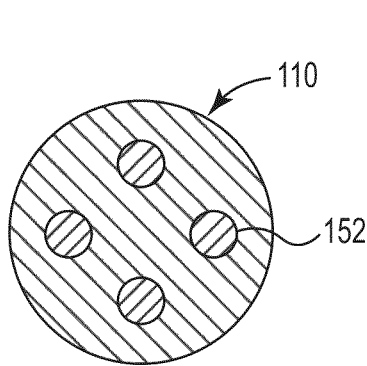
FIGS. 12A and 12B are end cross-section views of a portion of a lead, body provided in accordance with yet other embodiments of the present invention.
Figure 12B:
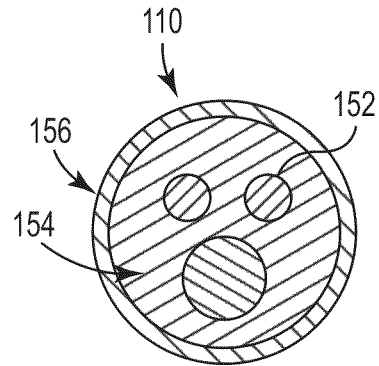
Figure 13:
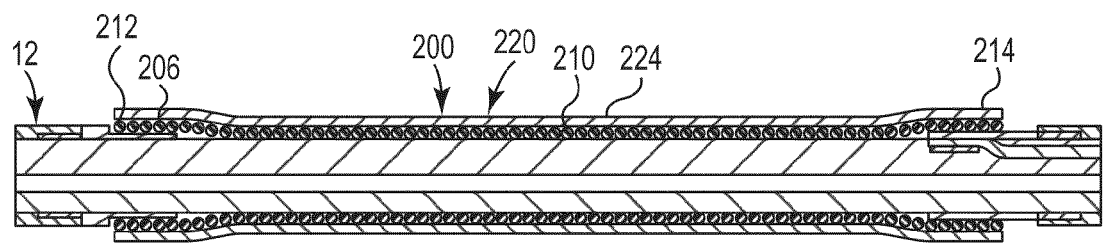
FIG. 13 is a longitudinal cross-sectional view of a portion of a lead body including a coiled electrode according to another embodiment of the present invention.

FIGS. 12A and 12B are cross-section views of a lead body 110 according to still other embodiments of the present invention. As shown in FIG. 12A, the lead body 110 is formed such that includes four lumens 152, although any number of lumens can be provided. In one embodiment, the lead body 110 is formed from a polyisobutylene urethane, urea or urethane/urea copolymer such as described above according to the various embodiments and can be either extruded or molded. As shown in FIG. 12B, the lead body 110 includes an inner core member 154 including multiple lumens 152 and at least outer tubular insulation layer 156. In some embodiments, both the inner core member 154 and the outer tubular insulation layer 156 can be formed from a polyisobutylene urethane, urea or urethane/urea copolymer such as described above. In another embodiment, only the outer tubular insulation layer 156 is formed from a polyisobutylene urethane, urea or urethane/urea copolymer.

According to some embodiments, various additional lead body components can be formed from a polyisobutylene urethane copolymers. For example, a polyisobutylene urethane copolymer having a high durometer (e.g. greater than about 85A) can be used to form those components traditionally constructed from material such as PEEK or Tecothane. In another embodiment, a polyisobutylene urethane copolymer can be molded over an existing lead body component. Such lead components include, but are not limited to: lead terminals, terminal pins, lead tips, portions of the header, and others. In another embodiment, a polyisobutylene urethane copolymer having a low durometer (e.g. less than about 60A) can be used to fabricate lead body components traditionally fabricated using silicone rubbers including but limited to: O-rings, seals, low traumatic tips or tip heads. In still another embodiment, a polyisobutylene urethane copolymer such as described above according to the various embodiments of the present invention can be used to construct various portions of a pulse generator to which the lead is connected including portions of the connectors and/or headers.

In certain embodiments of the invention, the outer surfaces of the lead body and/or lead body components formed from polyisobutylene urethane copolymers can be treated to increase their lubricity. For example, in one embodiment, the outer surfaces can be coated with a parylene layer or plasma grafted with a biocompatible monomer for this purpose, examples of which include hexamethylene disilazane, C3F8 (octafluoropropane), polyvinyl pyrollidone, trifluoromethane, octafluorocyclobutane and tetraglyme among others. For example, modification of the outer surface via plasma grafting with tetraglyme produces a polyethylene glycol like surface. Additional exemplary compounds and methods of treating the surfaces of the lead body and/or lead body components are shown and described in U.S. Provisional Application No. 61/098,450 filed on Sep. 19, 2008 entitled SURFACE MODIFICATION TO IMPROVE LUBRICITY, ABRASION RESISTANCE AND TEMPERATURE RESILIENCE OF LEADS which is incorporated herein by reference in its entirety.

According to some embodiments, the polyisobutylene urethane copolymers described above according to the various embodiments also can be used to provide a thin film covering over the outer surface of an electrode. FIG. 11 is a longitudinal cross sectional view of a portion of the lead body 12 including a coiled electrode 200 according to various embodiments of the present invention. The coiled electrode 200 is formed from at least one conductive filar 206 and has an outer surface 210 extending from a first end 212 to a second end 214. According to one embodiment, the coiled electrode 180 includes a polymeric cover 220 disposed over the outer surface 210 of the electrode 200 such that it extends from at least the first end 212 to the second end 214. In a further embodiment, the polymeric cover 220 can extend beyond the first and/or second ends 212, 214 of the coiled electrode. In one embodiment, the polymeric cover 220 has sufficient porosity so as to promote conductivity. In a further embodiment, the polymeric cover 220 has a degree of porosity that is large enough to support conductivity when wetted with an appropriate ionic fluid, but small enough to prevent tissue ingrowth. As such, a polymeric cover 220 formed from a polyisobutylene urethane, urea or urethane/urea copolymer such as described above according to the various embodiments may be used in place of the traditional GORE® electrode coverings used to cover coiled defibrillation electrodes.

The polymeric covering 220 includes one or more layers of a thin film 224 formed form a polyisobutylene urethane, urea or urethane/urea copolymer described above according to various embodiments of the present invention. Multiple layers of the thin film 224 can be wrapped about the outer surface 210 of the electrode 200 to achieve a desired thickness. A helical wrap or a cylindrical wrapping technique can be employed to wrap multiple layers of the polymeric thin film 224 to form the polymeric cover 220. In one embodiment, the polymeric covering 220 can be bonded to the outer surface of the lead body 12 which may also comprise the same or similar polymeric material. In another embodiment, the polymeric cover 220 can be bonded to a polymeric filler material that is disposed between gaps formed between the windings of the filar(s) used to form the coiled electrode. The polymeric filler material also can be formed from the same or similar material as the polymeric covering 220.

The thin film 224 used to form the individual layers of the polymeric cover 220 can be formed using a variety of techniques known to those of skill in the art. According to one embodiment of the present invention, an electrospinning technique can be used to form the thin film 224. Electrospinning of liquids and/or solutions capable of forming fibers, is known and is described, for example, U.S. Pat. No. 4,043,331 which is hereby incorporated by reference herein. Electrospinning produces a continuous web or matrix of fibers. In one embodiment, the fibrous matrix forming the thin film 224 can be directly onto the outer surface 210 of the electrode 200. In another embodiment, the fibrous matrix forming the thin film 224 first can be formed on a substrate, and then wrapped about or slid over the outer surface 220 of the electrode as described above. Due to the small diameters of the electrospun fibers, electrospun fiber matrices inherently possess a very high surface area and a small pore size. In a further embodiment, the fibrous matrix can be formed such that has a sufficient degree of porosity so as to promote conductivity.

In addition to the polyisobutylene urethane copolymers disclosed herein, the polymeric components for use in the medical devices of the present invention may optionally contain one or more supplemental agents. For example, in some embodiments, an organically modified silicate is provided as a supplemental agent. Such an agent may act to create a tortuous pathway for moisture thereby decreasing the moisture permeability of the polymeric component. Moreover, such silicates may maintain the strength and increase the modulus of the polymeric component. Supplemental agents further include agents such as alumina, silver nanoparticles, and silicate/alumina/silver nanoparticle composites and therapeutic agents (discussed in more detail below).

In embodiments where one or more therapeutic agents are provided, they may be positioned beneath, blended with, or attached to (e.g., covalently or non-covalently bound to) polymeric regions (e.g., lead components) in accordance with the invention. "Therapeutic agents," "drugs," "pharmaceutically active agents," "pharmaceutically active materials," and other related terms may be used interchangeably herein.

A variety of therapeutic agents can be employed in conjunction with the present invention including the following among others: (a) anti-inflammatory agents such as dexamethasone, prednisolone, corticosterone, budesonide, estrogen, sulfasalazine and mesalamine, (b) antimicrobial agents such as triclosan, cephalosporins, aminoglycosides and nitrofurantoin; (c) anesthetic agents such as lidocaine, bupivacaine and ropivacaine, (d) anti-proliferative agents such as paclitaxel, (e) immunosuppressants such as sirolimus, biolimus and everolimus, (f) anti-thromobogenic agents such as heparin, and (g) growth factors such as VEGF.

Where a therapeutic agent is present, a wide range of loadings may be used in conjunction with the medical devices of the present invention. Typical therapeutic agent loadings range, for example, from than 1 wt % or less to 2 wt % to 5 wt % to 10 wt % to 25 wt % or more of the polymeric region (e.g., lead component).

Moreover, in some embodiments, a part of the lead body or the complete lead body can be further coated with a lubricious coating, typically formed from a hydrophilic polymer or other material (e.g., poly(vinyl pyrrolidone), polyethylene/oligoethylene, polyHEMA, polytetraglyme, hyalorunic acid and its derivatives, chitosan and its derivatives, etc.), which material may be crosslinked, to reduce coefficient of friction.

Numerous techniques are available for forming polymeric regions in accordance with the present invention.

For example, where the polyisobutylene urethane copolymers of the invention have thermoplastic characteristics, a variety of standard thermoplastic processing techniques may be used to form polymeric regions from the same. Using these techniques, a polymeric region can be formed, for instance, by (a) first providing a melt that contains polymer(s) and any other optional agents such as silicates, therapeutic agents, and so forth, and (b) subsequently cooling the melt. Examples of thermoplastic processing techniques include compression molding, injection molding, blow molding, spraying, vacuum forming, calendaring, extrusion into sheets, fibers, rods, tubes and other cross-sectional profiles of various lengths, and combinations of these processes. Using these and other thermoplastic processing techniques, entire devices or portions thereof (e.g., device components) can be made.

Other processing techniques besides thermoplastic processing techniques may also be used to form the polymeric regions of the present invention, including solvent-based techniques. Using these techniques, polymeric regions can be formed, for instance, by (a) first providing a solution or dispersion that contains polymer(s) and any optional agents such as therapeutic agents, silicates and so forth, and (b) subsequently removing the solvent. The solvent that is ultimately selected will contain one or more solvent species, which are generally selected based on their ability to dissolve the polymer(s) that form the polymeric region, in addition to other factors, including drying rate, surface tension, etc. In certain embodiments, the solvent is selected based on its ability to dissolve or disperse the optional agents, if any. Thus, optional agents such as therapeutic agents, silicates, and so forth may be dissolved or dispersed in the coating solution. Solvent-based techniques include, but are not limited to, solvent casting techniques, spin coating techniques, web coating techniques, spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer containing melt (where thermoplastic processing is employed) is applied to a substrate to form a polymeric region. For example, the substrate can correspond to all or a portion of an implantable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device component is extruded. In another example, a polymeric coating layer is co-extruded along with and underlying medical device component. In another example, a polymeric tube is extruded which is then assembled over a medical device substrate (e.g., on an electrical lead, either as an electrically insulating or electrically non-insulating jacket).

As noted above, in various embodiments of the invention, a medical lead component (e.g., an elongated tubular component, elongated multi-lumen extrusion, etc.) is formed which varies in hardness or stiffness along its length. In some embodiments, such a component may be formed, for example, from previously formed components of differing hardness that are bonded to one another (e.g., by thermoplastic bonding, by using a suitable adhesive, etc.). In some embodiments, such a component may be formed by an extrusion operation in which the composition of the extruded component is varied during the course of the extrusion operation.

One example of such an extrusion operation is one in which previously formed polymers are fed into a single die from multiple polymer sources (e.g., using multiple feed screws), with each polymer source supplying a polymer that has a hardness that differs from the polymers supplied by the other sources. By varying the relative amount of copolymer that is supplied by each polymer source during the course of the extrusion, an extruded component of varying hardness (e.g., along its length, across its cross-section, etc.) can be produced.

Another example of such an extrusion operation is a reactive extrusion operation in which reactants (e.g., a polyisobutylene diol, a polyether diol such as polytetramethylene oxide diol and/or polyhexamethylene oxide diol, 1,4-butanediol diol, diisocyanate such as MDI and a suitable catalyst) are fed into an extruder using suitable flow controllers. Extruders of this type are described, for example, in U.S. Pat. No. 3,642,964 to Rausch Jr. et al. and U.S. Pat. No. 6,627,724 to Meijs et al. The extruder is operated at a temperature which promotes the polymerization process. The relative feed rates of each of the reactants can be varied over time to create an extrusion of varying hardness. The extruded polymer may be post-cured for reaction completion and may further be annealed for stress-relaxation.

EXAMPLES

Experimental

Materials

PTMO (TERATHANE® 1000 polyether glycol), 4,40-methylenebis(phenylisocyanate) (98%), toluene (99%), 1,4-butanediol (99%), hydrogen peroxide solution (30%), cobalt chloride hexahydrate (98%), and Triton® X-100 were used as received from Sigma-Aldrich (St. Louis, Mo.). $Sn(Oct)_2$ (stannous octoate, Polyscience, Niles, Ill.) and tetra-n-butyl-ammonium bromide (TBAB) (98+%, Alfa Aesar, Ward Hill, Mass.) were used as received. The control samples in this study consisted of PELLETHANE™ 2363-55D and PELLETHANE™ 2363-80A, received from Dow Chemical. Polyurethanes of varying hardness and PIB:PTMO compositions were synthesized as reported previously and are listed in Table I provided below.

TABLE 1

Polyurethane Nomenclature and Compositions

| Code | HO—PIB—OH[a] (wt % in SS) | HO—PTMO—OH[b] (wt % in SS) | SS:HS (wt:wt) | PTMO wt % in polymer | Shore A Hardness |
|---|---|---|---|---|---|
| 60A 82 | 80 | 20 | 79:21 | 16 | 60 |
| 60A 91 | 90 | 10 | 79:21 | 8 | 60 |
| 80A 73 | 70 | 30 | 65:35 | 19.5 | 80 |
| 80A 82 | 80 | 20 | 65:35 | 13 | 80 |
| 80A 91 | 90 | 10 | 65:35 | 6.5 | 80 |
| 100A 82 | 80 | 20 | 60:40 | 12 | 100 |
| 60A PIB | 100 | 0 | 79:21 | 0 | 60 |
| 60A 91 SAT | 90 | 10 | 79:21 | 8 | 60 |

[a]HO—PIB—OH, $M_n$ = 2200 Da.
[b]HO—PTMO—OH, $M_n$ = 1000 Da.

The two-stage process is described for a representative polyisobutylene urethane copolymer (60A 82) as follows: HO-Allyl-PIB-Allyl-OH ($M_n$=2200 Da, 5.2 g, 2.36 mmol) and PTMO ($M_n$=1000 Da, 1.3 g, 1.3 mmol), were dried by azeotropic distillation using dry toluene (10 mL). The mixture was kept at 45° C. for 3 hours under vacuum. Dry toluene (25 mL) was added followed by Sn(Oct)$_2$ (28.3 mg, 0.07 mmol) in toluene. The mixture was heated at 80° C. under a slow stream of dry nitrogen gas. Then MDI (1.76 g, 7.02 mmol) was added to the mixture and the mixture was stirred vigorously for 30 min. Finally BDO (302 mg, 3.36 mmol) was added and the mixture was stirred at 100° C. for 4 hours. The mixture was cooled to room temperature, poured into a Teflon mold and the solvent was evaporated at room temperature in air for 48 hours. Finally, the polymer was dried under vacuum at 50° C. for 12 hours. A polyisobutylene urethane copolymer without PTMO was prepared according to a process shown and described in Ojha et al. Syntheses and Characterization of Novel Biostable Polyisobutylene Based Thermoplastic Polyurethanes Polymer 2009; 50:3448-3457, which is incorporated herein by reference. The saturated PIB-PTMO polyurethane was synthesized using HO-propyl-PIB-propyl-OH, prepared using a method shown and described in Bela et al. *Living Carbocation Polymerization. XX. Synthesis of Allyl-Telechelic Polyisobutylenes by One-Pot Polymerization-Functionalization Polymer*. Mater. Sci. Eng. 1988; 58:869-872, which is incorporated herein by reference in its entirety.

The polyurethanes were compression molded using a Carver Laboratory Press model C (Wabash, Ind.) at a load of 16,000 lbs. at 160° C. They were molded into thin films ranging in thickness from 0.2 to 0.5 mm and cut into rectangular strips with approximate dimensions of 3 mm in width and 30 mm in length. The polyurethanes were characterized prior to accelerated degradation using $^1$H NMR and GPC. Some compositions (80A 91, 100A, 60A PIB) did not dissolve in the GPC eluent.

Labeling System

In this labeling system the first set of characters describe the Shore A hardness. The next two numbers denote the ratio of PIB:PTMO. Extra letters denote a polyurethane that is unique to the series of polyurethanes tested, such as PIB which indicates exclusively PIB in the SS, or SAT which indicates that the PIB precursor used contained the saturated hydroxypropyl versus the hydroxyallyl end groups. P55D and P80A refer to PELLETHANE™ 2363-55D and PELLETHANE™ 2363-80A, respectively.

In Vitro Oxidative Treatment

The samples were placed in vials and soaked in a 20% H$_2$O$_2$ in aqueous 0.1 M CoCl$_2$ solution and stored at 50° C. The solutions were changed every other day to ensure a steady concentration of radicals. At time points after 1, 2, 4, 6, and 12 weeks, dedicated samples were removed from the oxidative environment, washed seven times in aqueous 1% TRITON® X-100 surfactant solution, five times in ethanol, and five times in distilled water and dried under vacuum at 80° C. until constant weight.

Characterization

Dry samples were characterized by weight loss, ATR-FTIR spectroscopy, ultimate tensile strength, elongation at break, SEM, and GPC. The results of characterization are reported using n=3.

Example 1

Weight Loss

Figure 14:
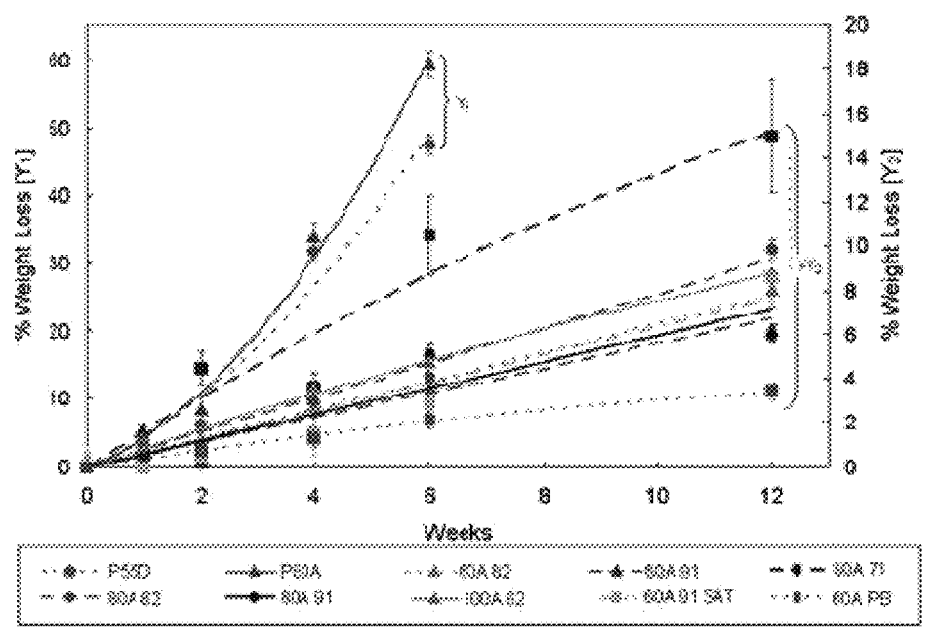
FIG. 14 is a plot of weight loss versus time for representative polyisobutylene urethane copolymer samples containing PTMO.

Weights were measured of dry polyurethane films before and after oxidative treatment on a Sartorius MC1 Analytic AC 210S balance (Elk Grove, Ill.). The weight loss plotted against time is shown in FIG. 14. The PIB-PTMO polyisobutylene urethane copolymers all show very low weight loss after 12 weeks ranging from values of 6-15% depending on the composition. Among the 60A batch, the 90/10 composition showed lower weight loss of 6% compared to 8% for the 80/20 composition. The 60A 91 SAT shows weight loss comparable to the unsaturated 60A 91. Similarly in the 80A batch, the polyisobutylene urethane copolymers with lower PTMO content showed lower weight loss, 15, 10, and 6% for 30, 20, and 10% PTMO, respectively. More specifically, the weight loss could be correlated to the PTMO content in the polyurethanes.

Figure 15:
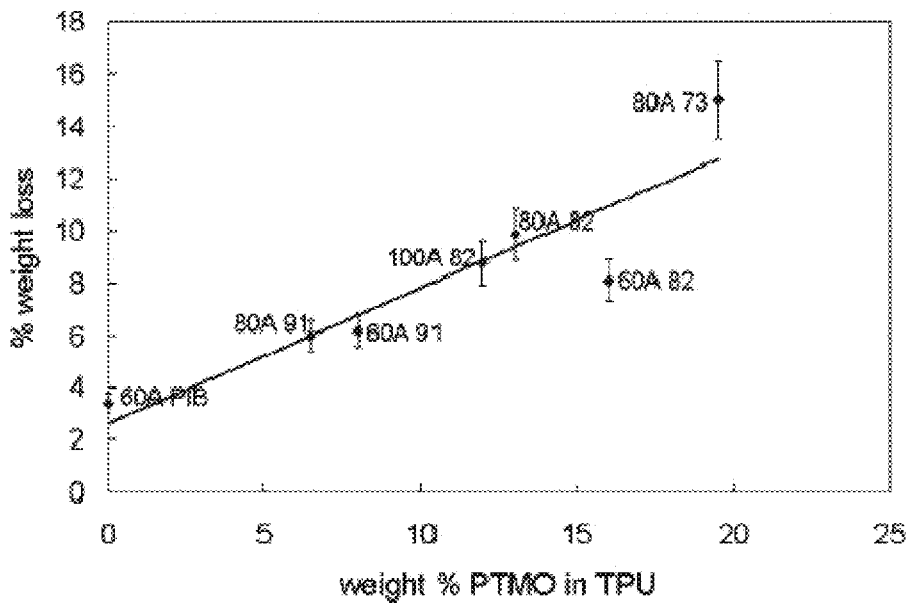
FIG. 15 is a plot of weight loss at 12 weeks versus PTMO content for representative polyisobutylene urethane copolymer samples.

In FIG. 15 weight loss at 12 weeks versus PTMO content is plotted. As can be seen for the PIB-PTMO polyisobutylene urethane copolymers there is approximately a linear relationship between the weight loss and the PTMO content. This discovery supports the notion that it is the polyether SS which degrades via MIO and it is these portions which are excised from the polyurethane. As shown in FIG. 15, 60A 82 showed a lower weight loss than expected for its PTMO content. The polyisobutylene urethane copolymer which contained only PIB also showed a small weight loss, which fits the plot. Since there is such a large surface area to volume ratio, we expect to see some small erosion from the surface. The PELLETHANE™ control samples showed noticeable weight loss even after 1 week in vitro, and P80A and P55D completely degraded after ~7 and 9 weeks, respectively. It is observed that P80A, containing more SS, loses weight more rapidly than P55D, which is consistent with the proposed mechanism of oxidation.

Example 2

ATR-FTIR

ATR-FTIR was performed on a Thermo Electron Corporation Nicolet 4700 FT-IR instrument (Waltham, Mass.) with a Thermo Electron Corporation Smart Orbit attachment for ATR with a diamond crystal. Thirty-two scans were averaged to obtain one representative spectrum for each sample. The respective dry clean polyisobutylene urethane copolymer strip was placed on the crystal, firmly secured using the foot attachment, and scanned for analysis. The region of interest was between ~1700 cm$^{-1}$ and ~1100 cm$^{-1}$, which includes HS degradation product (~1650 cm$^{-1}$), SS degradation moiety (~1110 cm$^{-1}$) and product (~1170 cm$^{-1}$) and the normalized reference peak (~1410 cm$^{-1}$).

ATR-FTIR analysis was performed to confirm the presence and progression of the MIO mechanism. In this mechanism, a hydroxyl radical abstracts a-hydrogen from the polyether segment. The resulting radical may combine with another chain radical to form a crosslink junction or react with another hydroxyl radical to form a hemiacetal. The hemiacetal oxidizes to ester which is subsequently hydrolyzed resulting in chain scission. Therefore progression of degradation can be observed by following the disappearance of the SS ether peak and/or the appearance of the crosslinking peak. All spectra were normalized to the peak at 1410 cm$^{-1}$, which corresponds to the aromatic C—C stretch of the hard segment.

Figure 16:
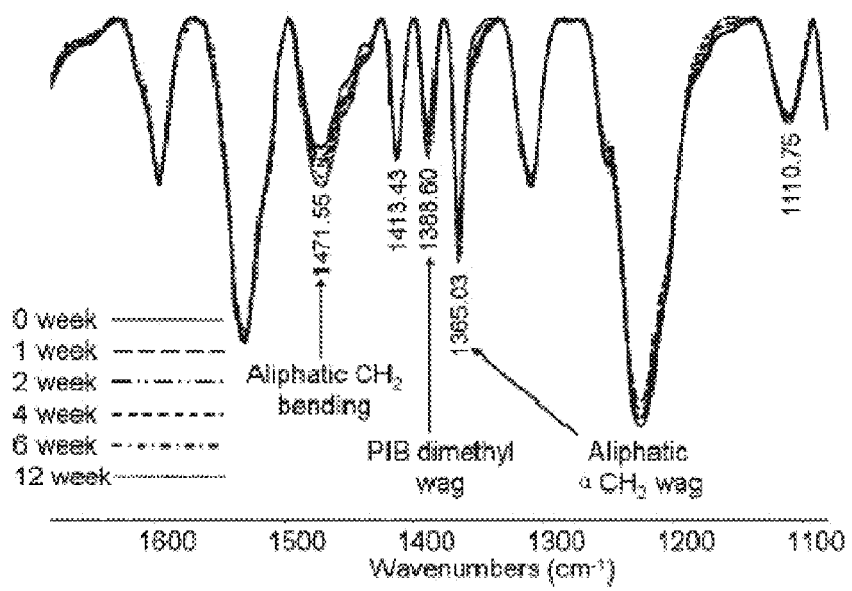
FIG. 16 is a representative FTIR spectrum of a polyisobutylene urethane copolymer containing PTMO.
Figure 17:
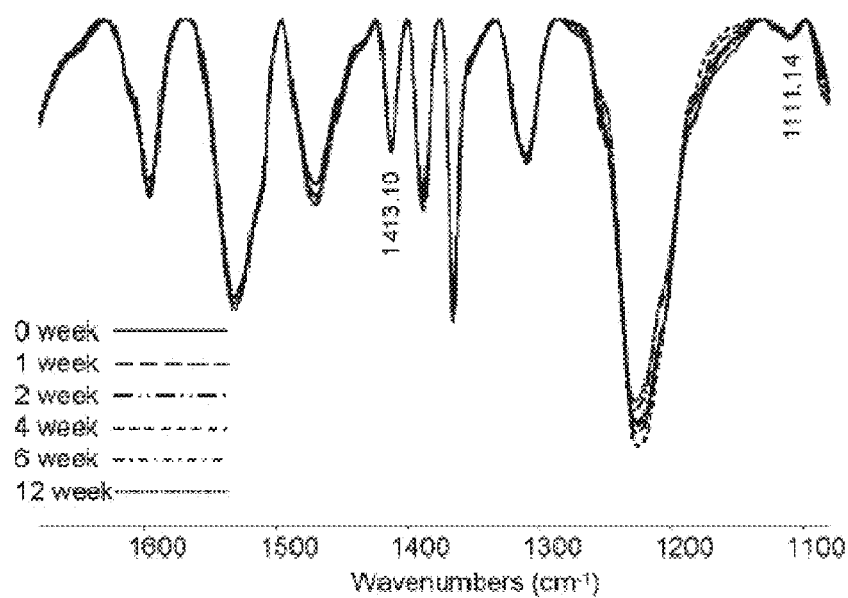
FIG. 17 is a representative FTIR spectrum of a polyisobutylene urethane copolymer including a saturated PIB diol.

The PIB-PTMO polyurethanes all show very small changes in the FTIR spectrum. A representative spectrum, that of 60A 82, is shown in FIG. 16. There is no appreciable change in the aliphatic ether C—O—C peak at 1110 cm$^{-1}$ and C—O—C branching peak at ~1174 cm$^{-1}$ is absent. However, an increase in the aliphatic peaks with time is observed (aliphatic CH$_2$ bending at 1470 cm$^{-1}$, PIB dimethyl wag at 1388 cm$^{-1}$, and aliphatic CH$_2$ wag at 1365 cm$^{-1}$). This behavior can be rationalized by migration of PIB segments to the surface during vacuum drying at 80° C. Since these peaks increase with time, it is suggested that the PIB is replacing PTMO on the surface (1-2 μm deep as observed by ATR-FTIR). Together with the weight loss and SEM data shown in FIGS. 14-15 and 24-25 it is concluded that there is some. PTMO degradation. In these PIB-PTMO polyisobutylene urethane copolymers cross-linking may be absent since there is not a significant presence or mobility of PTMO to allow two polymer radicals to combine before they are otherwise cleaved. Similar results are observed in the other PIB-PTMO spectra. The 60A 91 SAT batch was included in this study to determine if the unsaturated allyl moiety in the PIB diol was vulnerable to oxidation. The FTIR spectrum of the polyisobutylene urethane copolymer using the saturated diol appears identical to that of the polyisobutylene urethane copolymer containing unsaturated diol. Additionally the 60A PIB polyisobutylene urethane copolymer was included to confirm that there is only polyether SS degradation, and not HS degradation in these polyisobutylene urethane copolymers. These spectra are shown in FIG. 17. This hypothesis was confirmed as the spectrum shown in FIG. 17 shows no change at all. There is no change in the PIB peak at 1388 cm$^{-1}$ or ether peak at 1111 cm$^{-1}$ since there is no polyether to be degraded. There is also no evidence of HS T2 degradation. Table 2, shown below, lists the IR peaks where trends of change were observed.

TABLE 2

Assigned ATR-FTIR Spectral Peak Changes

| Wave Number (cm$^{-1}$) | Proposed Peak Assignment | P80A | P55D | PIB—PTMO |
|---|---|---|---|---|
| 1637 | NH$_2$ aromatic amine | X | — | — |
| 1476 | Aliphatic CH$_2$ bend | — | — | X |
| 1388 | PIB CH$_3$ wag | — | — | X |
| 1365 | Aliphatic α—CH$_2$ wag | X | X | X |
| 1173 | C—O—C branching | X | X | — |
| 1110 | Aliphatic C—O—C | X | X | — |

Figure 18:
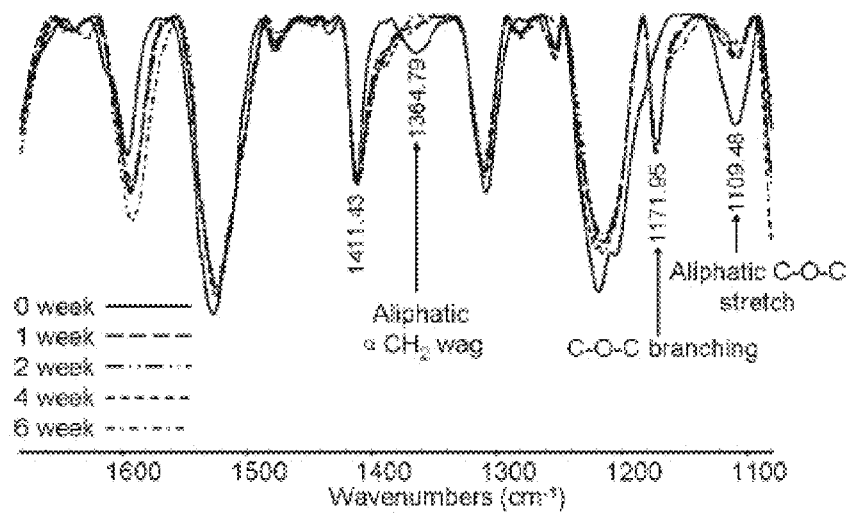
FIGS. 18 and 19 are FTIR spectra of representative PELLATHANE™ samples.
Figure 19:
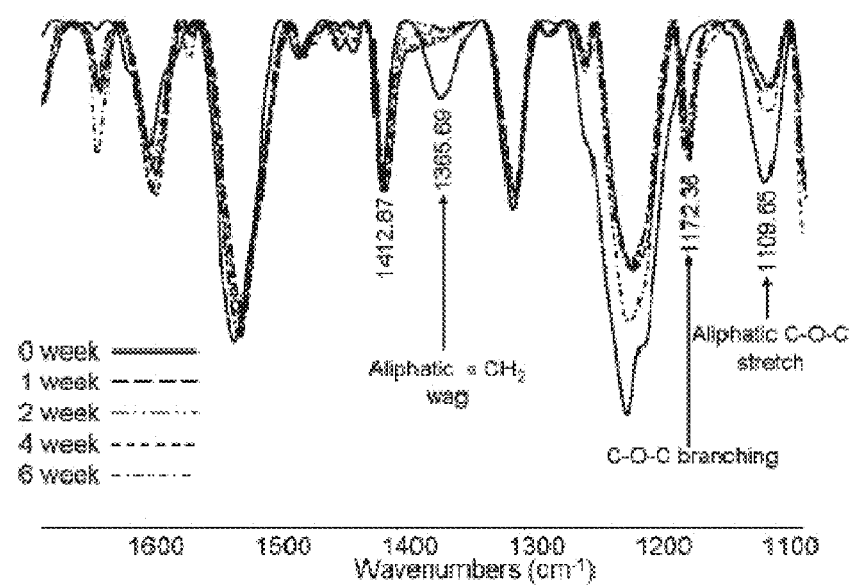

The PELLETHANE™ samples showed the expected behavior as is consistent with the weight loss data as well as previous studies. The spectra of P55D are shown in FIG. 18 The spectrum shown in FIG. 18 exhibits a significant decrease in the aliphatic C—O—C peak at 1109 cm$^{-1}$ after 1 week, then more slowly until 6 weeks. Concurrently, we observe a rapid disappearance of the aliphatic a-CH$_2$ peak at 1364 cm$^{-1}$ after just 1 week. Also the C—O—C branching peak at 1172 cm$^{-1}$ is observed immediately at 1 week, then stays constant in magnitude. As it will be seen later, the PELLETHANE™ samples continued to degrade at a constant, if not accelerated rate after 1 week, and so an explanation is in order for the IR spectra. ATR-FTIR is a surface characterization technique and degradation is expected to begin at the surface. Therefore we conclude that the segments vulnerable at the surface are oxidized almost immediately and deeper oxidation occurs in the following weeks as observed from the rest of the analyses. The ATR-FTIR spectra of P80A are shown in FIG. 19, and show very similar results. The magnitudes of the differences in the ether and crosslinking peaks are different than in P55D. The tensile data indicates (see later) that chain scission had a predominant effect on P55D over crosslinking, whereas P80A was affected greatly by both crosslinking and chain scission in turn.

Example 3

GPC

Molecular weights and molecular weight distributions were measured with a Waters HPLC system equipped with a model 510 HPLC pump, model 410 differential refractometer, model 441 absorbance detector, online multi-angle laser light scattering (MALLS) detector (Mini-Dawn, Wyatt Technology, Santa Barbara, Calif.), Model 712 sample processor, and five Ultrastyragel GPC columns (Waters, Milford, Mass.) connected in the following series: 500, 103, 104, 105, and 100 Å. A hydrogen bond disruptor, tetra-n-butyl ammonium bromide (TBAB), was dissolved in THF (2% by weight) and used to dissolve the polyisobutylene urethane copolymers. The solution of THF:TBAB (98:2, wt:wt) was used as a carrier solvent with a flow rate of 1 mL min$^{-1}$.

The polyisobutylene urethane copolymer samples were dissolved in the carrier solvent of THF:TBAB (98:2, wt:wt). However, some compositions could not be dissolved. Comparison of the GPC results of the as-synthesized polymer and that of compression molded, untreated films (0 weeks), indicates that there is some crosslinking or other thermal degradation occurring during processing at elevated temperatures. Nevertheless, such minute changes did not seem to affect the properties of the polyisobutylene urethane copolymers.

Figure 20:
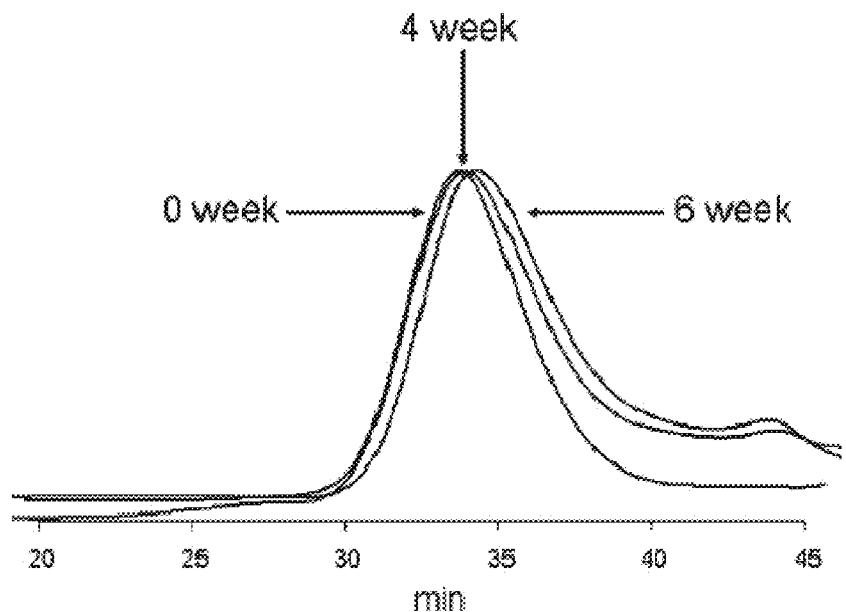
FIGS. 20 and 21 are GPC refractive index traces of representative PELLATHANE™ samples.

FIG. 20 shows the refractive index traces of P55D. The number average molecular weight (M$_n$) shows a decrease from 122 kDa at 0 weeks to 47 kDa at 4 weeks, and then 37 kDa at 6 weeks, while the molecular weight distribution (MWD) increases from 1.6 at 0 weeks to 3.0 at 6 weeks.

Figure 21:
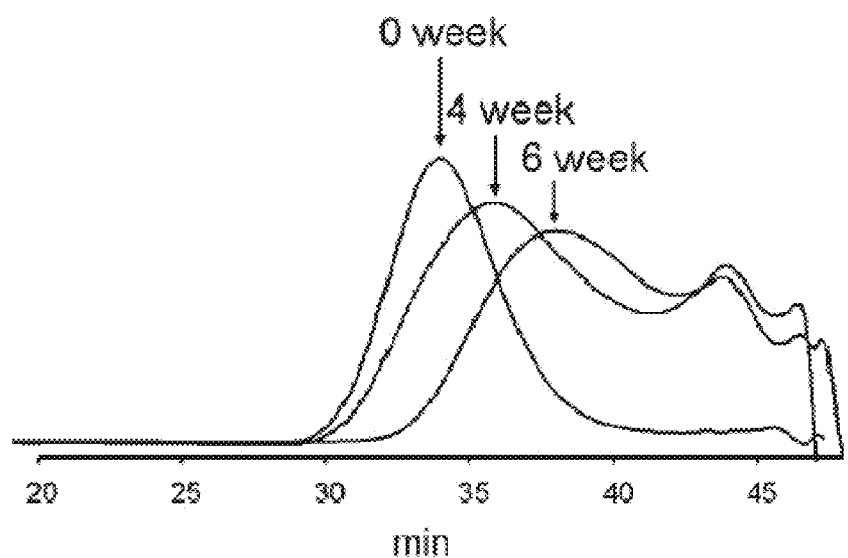

In FIG. 21 the refractive index traces of P80A are shown. M$_n$ shows a clear trend decreasing from 84 kDa before treatment to 18 kDa at 4 weeks and 14 kDa at 6 weeks. There is a clearly visible rise in some low molecular weight degradation product(s) by 4 weeks. Simultaneously there is an increase in the MWD. These findings are in agreement with the ATR-FTIR, weight loss, and tensile results.

Figure 22:
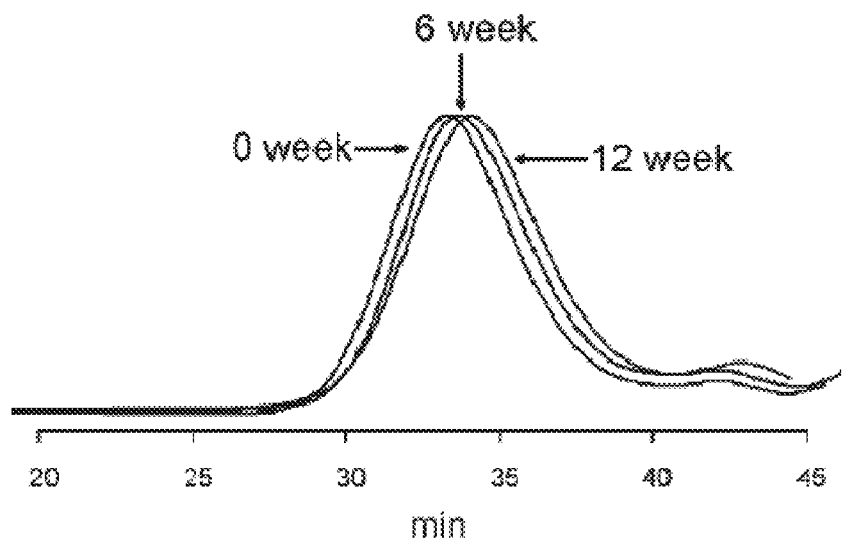
FIG. 22 is a representative GPC refractive index trace for a representative polyisobutylene urethane copolymer containing a saturated PIB diol.

GPC refractive index traces are shown FIG. 22 for 60A 91 SAT. The loss in molecular weight is minimal in agreement with the weight loss and tensile data. M$_n$ decreases slightly from 130 to 112 kDa after 6 weeks, then negligibly to 110 kDa at 12 weeks while the MWD remained unchanged at 1.6.

Example 4

Mechanical Testing

Tensile testing was performed at room temperature and atmospheric conditions with a 50 lb. load cell on an Instron Model Tensile Tester 4400R (Norwood, Mass.) at 50 mm min$^{-1}$ extension rate until failure. Ultimate tensile strength and elongation at break were recorded.

Figure 23:
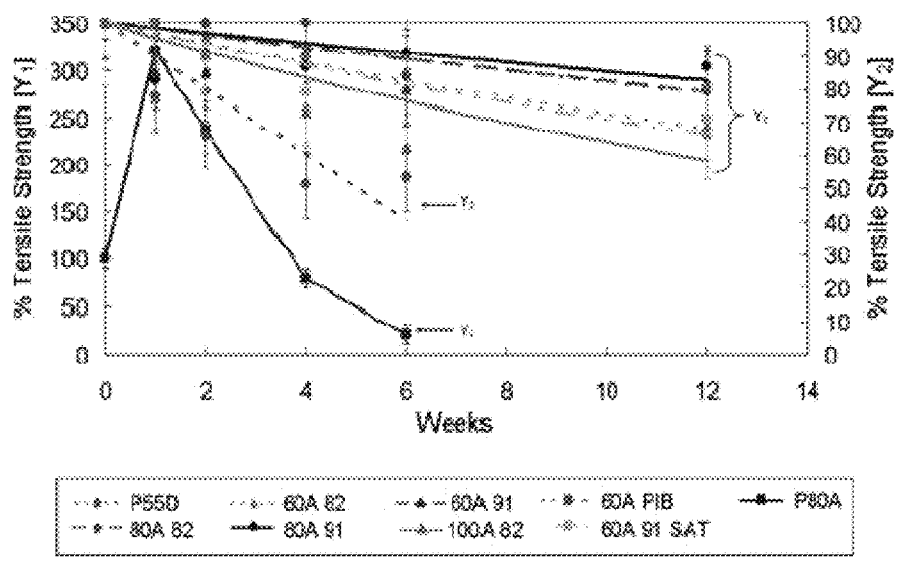
FIG. 23 is a plot of tensile strength versus time for various representative samples.

Tensile strength is plotted as a percentage of the original untreated sample versus time in FIG. 23. A drastic difference in the plots for the PELLETHANE™ urethane copolymers versus the PIB-PTMO polyisobutylene urethane copolymers is observed. Additionally, in the PIB-PTMO polyisobutylene urethane copolymers a minimal decrease in tensile strength is observed for all samples, although the rate of tensile loss varies for the different samples. The PIBPTMO polyisobutylene urethane copolymers show differing losses which are roughly correlated to the PTMO content. Among the 60A batch, the tensile losses from the different compositions are comparable. The 12-week data point for the 60A 91 could not be obtained because of a poor sample set. Nevertheless, the trend observed up to 6 weeks follows very closely that of the 60A 91 SAT. Minimal decrease in tensile strength was also observed in the 60A PIB sample, which showed no degradation as evident from weight loss and FTIR studies, discussed above. This indicates that 1-2 MPa may be within experimental error with the load cell and instrument used. Among the 80A batch the 80/20 composition shows ~21% drop in tensile strength, whereas the 90/10 composition shows only a decrease of ~13%. The 80A 73 sample (not shown here) demonstrated an initial increase in tensile strength, then subsequently a slower decrease. This is attributed to crosslinking initially, followed by chain scission consistent with the increased amount of PTMO in this sample. At this amount of PTMO (19.5% of total polyisobutylene urethane copolymer), there are sufficient concentration of chain radicals such that crosslinking as well as chain scission may occur. Although the % tensile strength at 12 weeks is greater than the other PIB-PTMO polyisobutylene urethane copolymers, extrapolation of the data would predict that the tensile strength 80A 73 would drop more sharply at longer time intervals. P55D shows greater resistance to degradation compared to P80A due to higher crystallinity. Thus the 100A 82 composition is expected to have comparable if not better strength than the 80A 82 composition, yet we see greater tensile drop. This may suggest that PIB is a better protector of the surface than the hard segment. Some of the samples actually show inhibition periods wherein the tensile strength does not begin to decrease until 2, 4, or even 6 weeks (esp. 80A 82). The ultimate elongation of the PIB-PTMO polyisobutylene urethane copolymers did not change significantly over the course of the treatment. The PELLETHANE™ samples again showed expected MIO behavior. P55D showed gradual tensile loss over time up to 6 weeks, and at 12 weeks there was no sample to test, as the samples had fractured in vitro. P80A showed an initial increase in tensile strength after 1 week, then a rapid decrease and had fractured before 12 weeks. This is explained by crosslinking of the chains initially, with chain scission occurring afterward as was observed with 80A 73. Since ATR-FTIR results indicate that in P55D crosslinking is also present, it is inferred that chain scission is the dominant oxidative route under these conditions. It was also observed that the modulus of the PELLETHANE™ samples increased with time approximately linearly, indicating crosslinking, consistent with the IR data, whereas the modulus of the PIB-PTMO polyisobutylene urethane copolymers remained stable.

Example 5

SEM

Portions of the dry treated films were isolated for SEM analysis. Surface morphology was observed on gold sputter-coated samples using a Denton Vacuum Desk IV Cold Cathode Sputter Coater (Moorestown, N.J.). The samples were sputter-coated for 1.5 min at 25% power, corresponding to a thickness of ~75 Å of gold. The coated samples were observed using a JEOL model JSM 7401F field emission scanning electron microscope (Peabody, Mass.). Several representative pictures were taken at 30× and 300× magnification.

Figure 24:
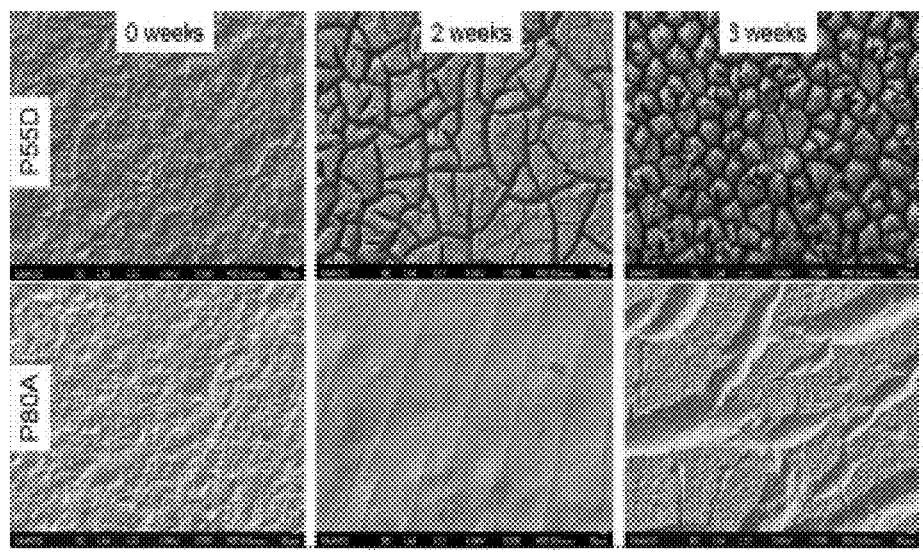
FIG. 24 shows scanning electron microscope (SEM) photos taken at 300× magnification of representative PELLETHANE™ samples.
Figure 25:
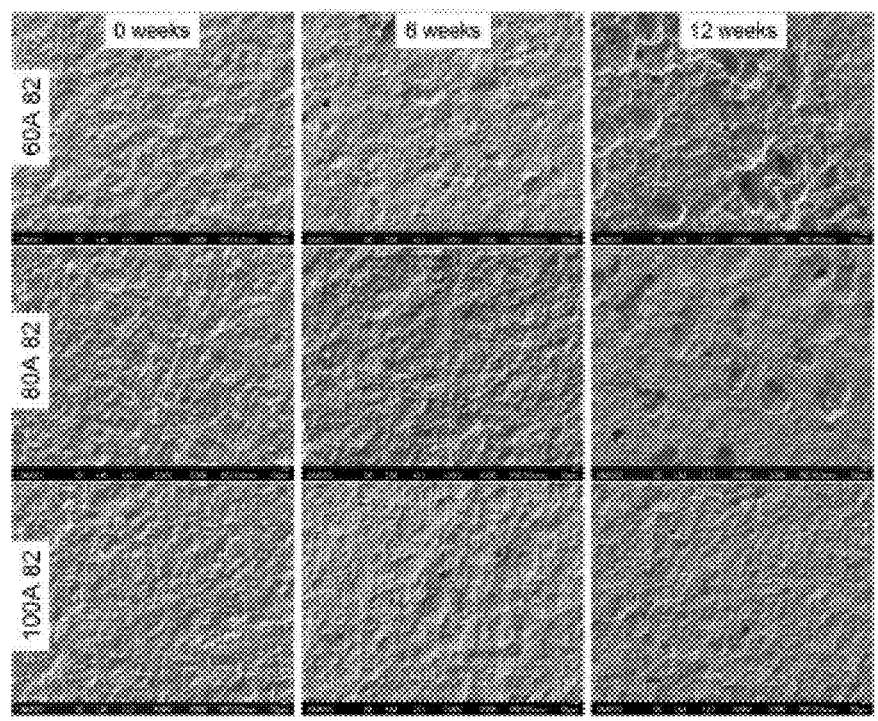
FIG. 25 shows scanning electron microscope (SEM) photos taken at 300× magnification of representative polyisobutylene urethane copolymer samples.

Representative SEM pictures taken at 300× magnification are shown in FIGS. 24 and 25 Shown in FIG. 24 are the PELLETHANE™ samples, which show the well observed behavior of surface degradation with treatment time. The surface density of cracks increases with time, and the visual inspection affirms the previous data as well. In FIG. 25, scanning electron micrographs of the 80/20 compositions are shown with different hardness to depict the effect of HS on the surface morphology. The responses of these polyisobutylene urethane copolymers to degradation are certainly different than the PELLETHANE™, but a trend of increasing surface imperfections with increasing SS content can be seen. The 60A 82 shows some pitting after 12 weeks, 80A 82 shows less pitting, and 100A 82 shows essentially no change in the surface morphology after 12 weeks. Some small holes are often observed in various samples, but these are not expected to be due to degradation. The same patterns were observed in the 60A PIB samples, which did not degrade; therefore such holes are expected to be an artifact of the compression molding process.

Example 6

Degradation Testing

Biostability testing under strain was also carried out on various samples including PELLETHANE™ 80A, PELLETHANE™ 55D, ELASTEON E2A; and PIB-PU 80A. The composition of the PIB-PU 80A sample used in this evaluation is shown below in Table 4.

TABLE 3

| PIB-PU 80A | | | | |
|---|---|---|---|---|
| HO—PIB—OH[a] (wt % in SS) | HO—PTMO—OH[b] (wt % in SS) | SS:HS (wt:wt) | PTMO wt % in polymer | Shore A Hardness |
| 80 | 20 | 65:35 | 13 | 80 |

[a]HO—PIB—OH, $M_n$ = 2200 Da.
[b]HO—PTMO—OH, $M_n$ = 1000 Da.

In this test, the samples were subjected to accelerated metal ion oxidation and environmental stress cracking. To conduct the study, the samples are strained to 150% and then left in the corrosive and oxidizing $CoCl_2/H_2O_2$ solution for 15 weeks at 50° C. under strain. The solutions were changed every other day to ensure a steady concentration of radicals. The samples are removed from the solution every three weeks and tested for loss in mass (degradation); tensile loss, change in molecular weight and surface erosion.

Figure 26:
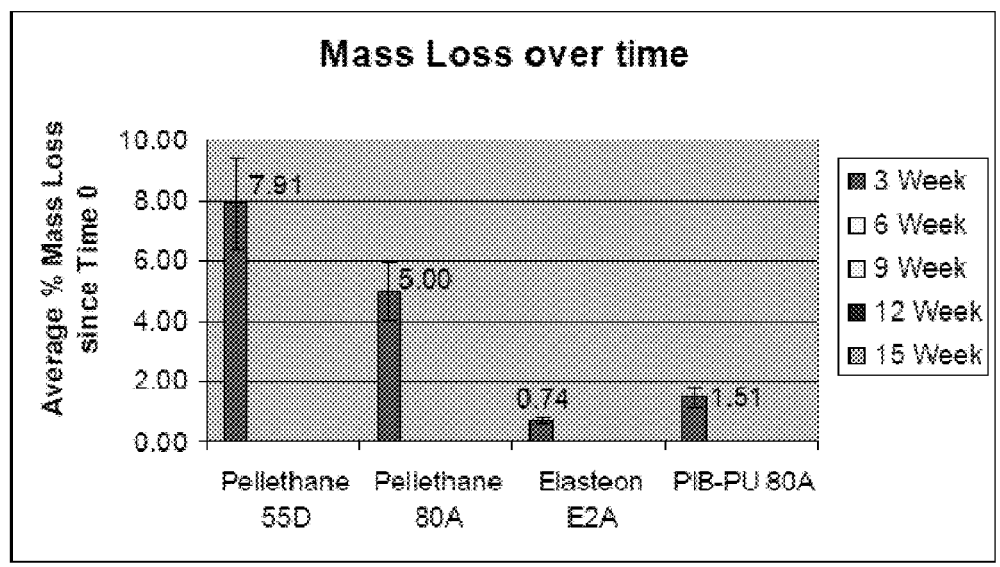
FIGS. 26 and 27 are bar graphs showing the loss in mass (degradation) at 3 weeks and at 6 weeks for various test samples.
Figure 27:
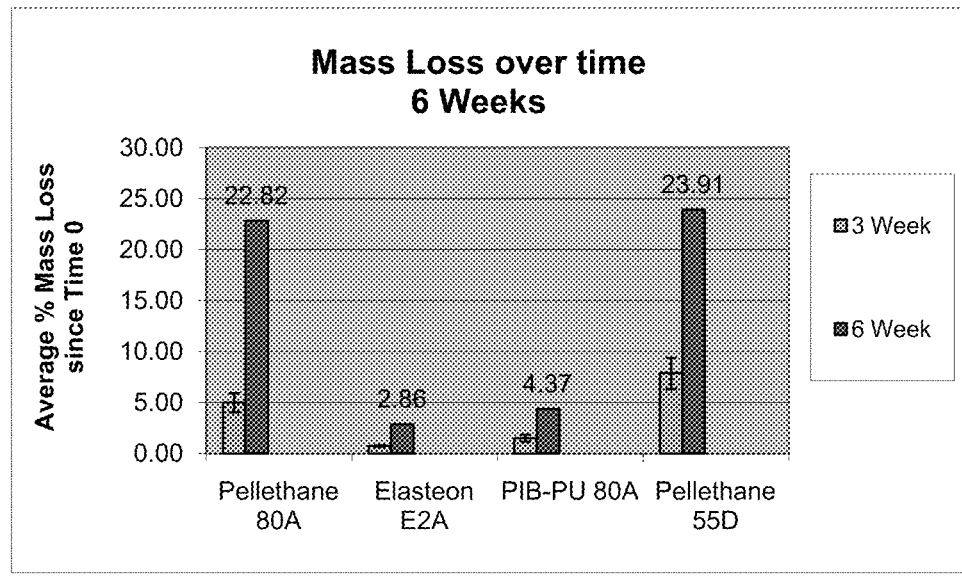
Figure 28:
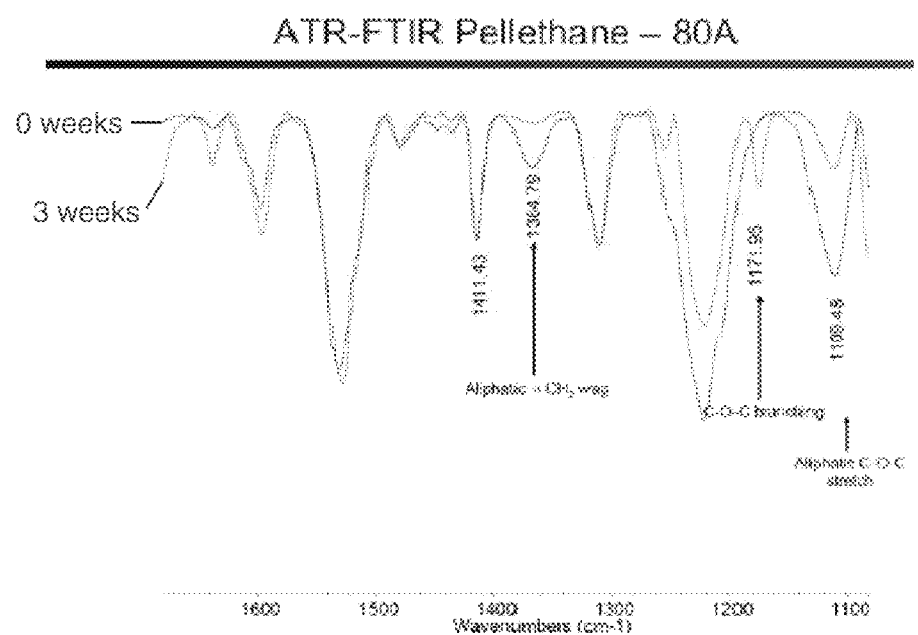
FIGS. 28-29 show FTIR spectra of two representative PELLATHANE™ samples subjected to accelerated degradation testing taken at 0 weeks and 3 weeks.
Figure 29:
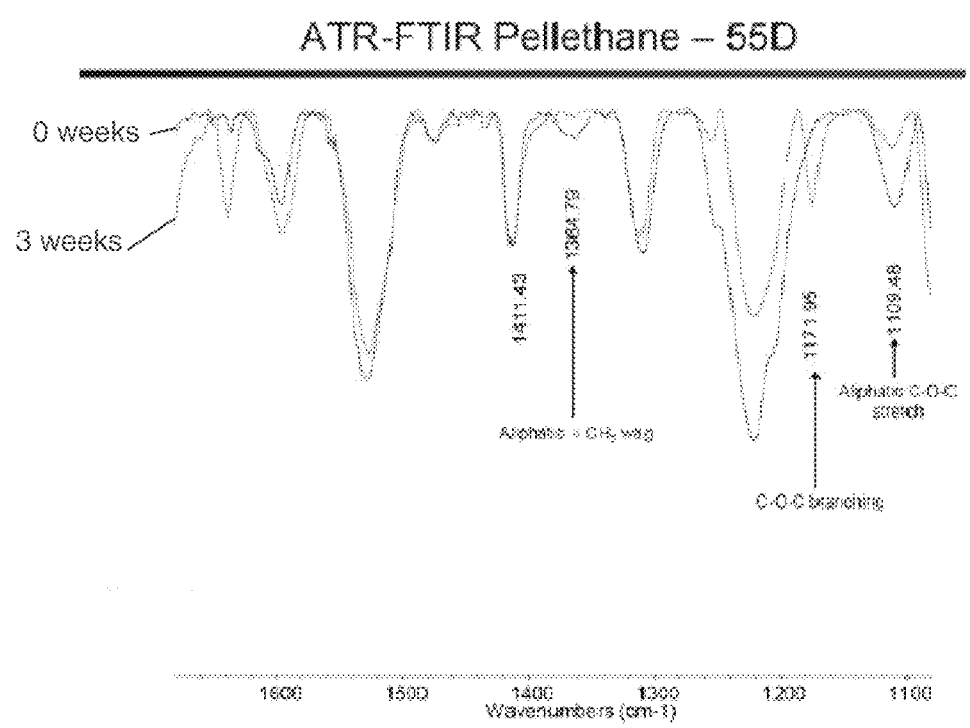
Figure 30:
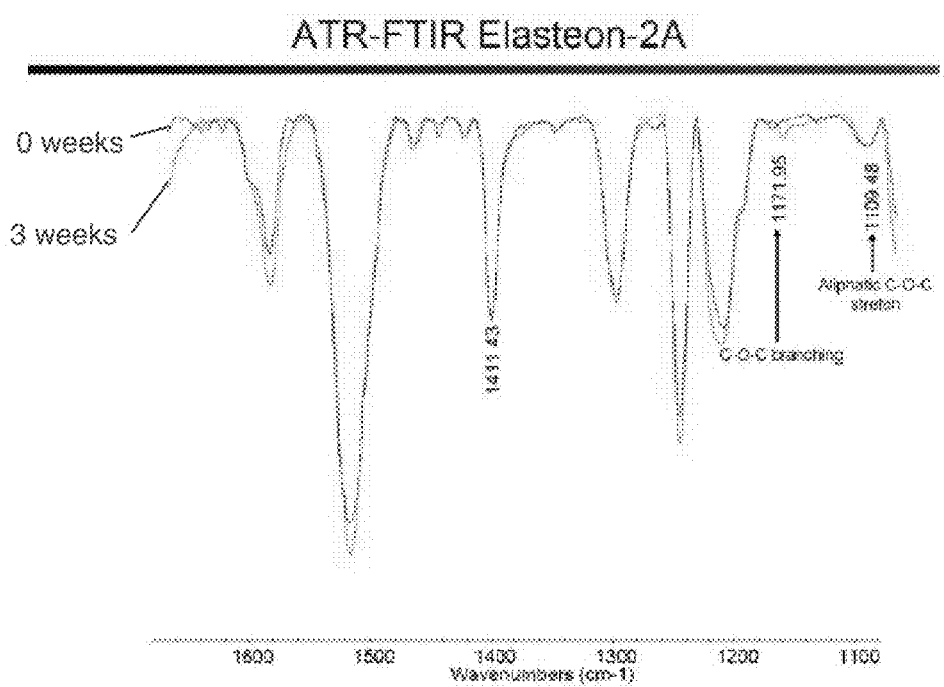
FIG. 30 shows FTIR spectra of an ELASTEON sample subjected to accelerated degradation testing taken at 0 weeks and 3 weeks.
Figure 31:
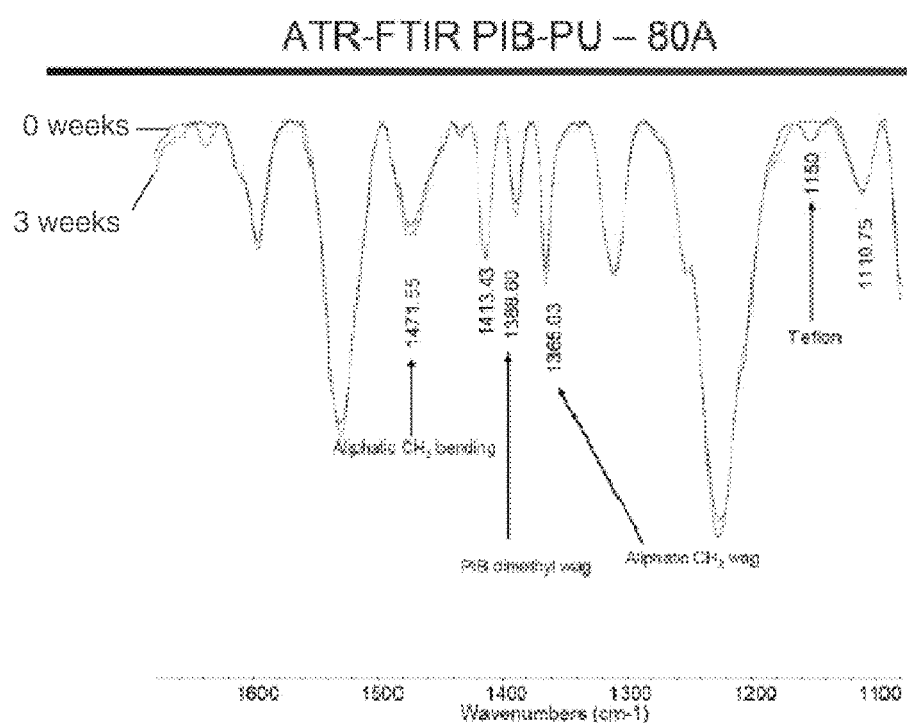
FIG. 31 shows FTIR spectra of a representative PI-PU sample subjected to accelerated degradation testing at 0 weeks and 3 weeks.

FIGS. 26 and 27 are bar graphs showing the loss in mass (degradation) at 3 weeks and at 6 weeks. At 3 and 6 weeks, PELLETHANE™ 80A and PELLETHANE™ 55D showed the greatest average percent mass loss. At 3 weeks ELASTEON E2A and the PIB-PU 80 sample showed a 0.74% and a 1.51% average loss in mass, respectively. At 6 weeks, ELASTEON E2A and the PIB-PU 80 samples showed approximately a 3% and a 4% average loss, respectively.

The tensile loss results for each of the samples at 3 weeks are summarized in Table 3, presented below.

TABLE 4

| Tensile Loss | | | | | |
|---|---|---|---|---|---|
| Polymer | Spec. No. | Break location | Ultimate Tensile Strength | % Elongation | % Tensile Loss |
| P-80A | 1 | g | 31 | 360 | |
| | 2 | g | 24 | 340 | |
| | 3 | g | 32 | 360 | |
| AVG | | | 29 | 354 | 56.06 |
| P-55D | 14 | t | 45 | 186 | |
| | 15 | t | 39.5 | 175 | |
| | 16 | t | 42 | 214 | |
| AVG | | | 42.17 | 192 | 15.67 |
| E2A | 5 | t | 29.2 | 438 | |
| | 6 | g | 14 | 242 | |
| | 7 | g | 26 | 387 | |
| AVG | | | 27.6 | 413 | 8 |
| PIB—PU | 9 | t | 21 | 280 | |

TABLE 4-continued

Tensile Loss

| Polymer | Spec. No. | Break location | Ultimate Tensile Strength | % Elongation | % Tensile Loss |
|---|---|---|---|---|---|
| | 10 | g | 26 | 304 | |
| | 11 | g | 23 | 345 | |
| | 12 | g | 31 | 380 | |
| AVG(10, 11, 12) | | | 26.67 | 343 | 8.05 |

PELLATHANE™ 80A exhibited approximately a 56% loss in tensile strength after 3 weeks. PELLATHANE™ 55D showed approximately a 16% loss in tensile strength. The results for both ELASTEON E2A and PIB-PU 80 were comparable. The ELASTEON E2A and PIB-PU 8-samples both showed an 8% loss of tensile strength.

The samples were also evaluated using ATR-FTIR. FIGS. 28-31 show representative FTIR spectra taken at 0 weeks and 3 weeks for each sample undergoing evaluation. Consistent with the previous testing results, discussed above, the spectra obtained for the PELLATHANE™ 80A and PELLATHANE™ 55D samples indicated the greatest amounts of degradation after three weeks.

Figure 32:
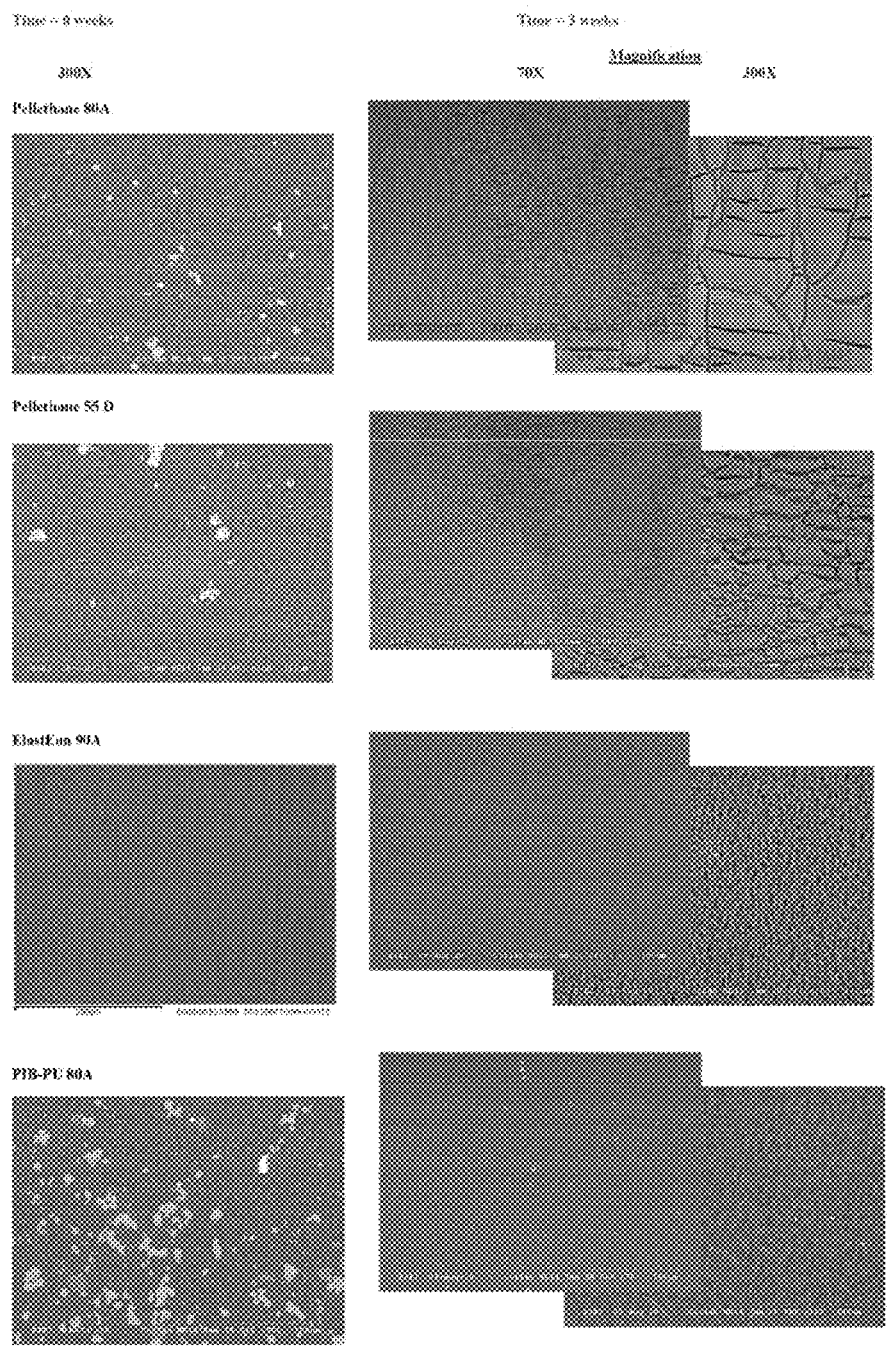
FIG. 32 shows comparative scanning electron microscope (SEM) photos of various test samples subjected to accelerated degradation testing taken at 0 weeks and 3 weeks.

The samples were also evaluated using SEM. Comparative SEM photos of each of the samples were taken at 0 weeks and 3 weeks and are shown in FIG. 32. The PELLETHANE™ samples represented in the top two images showed cracking and surface degradation at 3 weeks. The ELASTEON E2A and PIB-PU samples, represented in the third and fourth images, respectively, exhibited minimal surface degradation at 3 weeks.

Although various embodiments are specifically illustrated and described herein, it will be appreciated that modifications and variations of the present invention are covered by the above teachings and are within the purview of the appended claims without departing from the spirit and intended scope of the invention.

We claim:

1. An implantable medical lead comprising:
an elongated lead body comprising a lumen, at least one conductor disposed within the lumen and at least one electrode operatively coupled to the conductor and disposed along the lead body, wherein the lead body has a Shore hardness from about 30A to about 75D and comprises a polyisobutylene urethane, urea or urethane/urea copolymer comprising soft polymer segments and hard polymer segments;
wherein the soft polymer segments comprise a polyisobutylene segment and at least one additional polymer segment comprising a residue of: a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol; and
wherein a weight ratio of soft segments to hard segments in the copolymer ranges from 50:50 to 90:10.

2. The implantable medical lead according to claim 1, wherein a weight ratio of polyisobutylene to additional polymer ranges from about 70:30 to about 90:10.

3. The implantable medical lead according to claim 1, wherein the soft segments comprise a polyisobutylene segment and a residue of a polyether diol.

4. The implantable medical lead according to claim 1, wherein the soft segments comprise a polyisobutylene segment and a residue of a polyether diol, and wherein the polyether diol comprises a polytetramethylene oxide diol.

5. The implantable medical lead according to claim 4, wherein a weight ratio of polyisobutylene to polytetramethylene oxide diol ranges from about 70:30 to about 90:10.

6. The implantable medical lead according to claim 1, wherein the polyisobutylene segment comprises a residue of a saturated polyisobutylene diol.

7. The implantable medical lead of claim 1 wherein the lead body comprises an inner lumen and an inner surface of the lumen comprises the copolymer.

8. The implantable medical lead according to claim 7, wherein the conductor is a coiled conductor having a co-radial configuration and wherein the inner surface is disposed over an outer surface of the coiled conductor.

9. The implantable medical lead according to claim 1, wherein the lead body comprises an inner tubular layer and an outer tubular layer, wherein at least one of the inner and outer tubular layers comprises a polyisobutylene urethane, urea or urethane/urea copolymer.

10. The implantable medical lead according to claim 9, wherein the lead comprises first and second coiled conductors having a co-axial configuration, wherein the inner tubular layer is disposed between the first and the second conductors, and wherein the outer tubular layer is disposed over the second coiled conductor.

11. The implantable medical lead according to claim 1, wherein the lead body comprises a Shore hardness between about 30A and 100A.

12. An implantable medical lead comprising:
an elongated lead body comprising a lumen, at least one conductor disposed within the lumen and at least one electrode operatively coupled to the conductor and disposed along the lead body, wherein the lead body comprises a polyisobutylene urethane, urea or urethane/urea copolymer in each of a proximal region comprising a first Shore hardness, a middle region comprising a second Shore hardness and a distal region comprising a third Shore hardness;
wherein the copolymer comprises soft polymer segments and hard polymer segments and wherein the soft polymer segments comprise a polyisobutylene segment and at least one additional polymer segment comprising a residue of: a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol.

13. The implantable medical lead according to claim 12, wherein the distal region comprises a Shore hardness from about 30A to about 70A.

14. The implantable medical lead according to claim 12, wherein the middle region comprises a Shore hardness from about 60A to about 85A.

15. The implantable medical lead according to claim 12, wherein the proximal region comprises a Shore hardness from about 85A to about 100A.

16. The implantable medical lead according to claim 12, wherein the lead body further comprises one or more transition regions adjacent the proximal, middle or distal regions, and wherein transition regions have a different shore hardness than the adjacent proximal, middle or distal region.

17. The implantable medical lead according to claim 12, wherein the soft segment in each region comprises a residue of a polyether diol and wherein the polyether diol comprises a polytetramethylene oxide diol.

18. The implantable medical lead according to claim 17, wherein a weight ratio of polyisobutylene to polytetramethylene oxide in each region ranges from about 70:30 to about 90:10.

19. The implantable medical lead according to claim 12, wherein a weight ratio of soft segments to hard segments in the copolymer in each region ranges from 50:50 to 90:10.

20. The implantable medical lead according to claim 12, wherein the proximal region comprises a first weight ratio of soft segments to hard segments in the polyisobutylene urethane, urea or urethane/urea copolymer, the middle region comprises a second weight ratio of soft segments to hard segments in the polyisobutylene urethane, urea or urethane/urea copolymer, and the distal region comprises a third weight ratio of soft segments to hard segments in the polyisobutylene urethane, urea or urethane/urea copolymer.

21. An implantable medical lead comprising:
a flexible, elongated lead body comprising an inner tubular member including at least one longitudinal lumen therethrough;
at least one conductor extending through the at least one lumen of the inner tubular member, the conductor including an electrode having an exposed surface relative to the lead body; and
at least one polymeric component connected to at least one of the lead body, conductor and electrode, the at least one polymeric component comprising a polyisobutylene urethane, urea or urethane/urea copolymer, wherein the copolymer comprises soft polymer segments and hard polymer segments and wherein the soft polymer segments comprise a polyisobutylene segment and at least one additional polymer segment comprising a residue of: a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol.

22. The implantable medical lead according to claim 21, wherein the at least one polymeric component comprises a lead terminal, terminal pin, a lead tip, O-ring, seal or a header.

23. The implantable medical lead according to claim 21, wherein the at least one polymeric component comprises a thin film disposed on or adjacent to the exposed surface of the electrode.

24. The implantable medical lead according to claim 23, wherein the thin film comprises a plurality of electrospun fibers comprising the polyisobutylene urethane, urea or urethane/urea copolymer.

25. The implantable medical lead according to claim 23, wherein the thin film is disposed on a portion of the conductor.

26. The implantable medical lead according to claim 21, wherein the at least one polymeric component comprises a polymer tube disposed adjacent to the exposed surface of the electrode.

* * * * *